(12) United States Patent
Davies

(10) Patent No.: US 7,550,588 B2
(45) Date of Patent: Jun. 23, 2009

(54) HOMOTROPANES WITH CENTRAL NERVOUS SYSTEM ACTIVITY

(75) Inventor: Huw M. L. Davies, E. Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 1 day.

(21) Appl. No.: 11/716,816

(22) Filed: Mar. 12, 2007

(65) Prior Publication Data

US 2007/0232587 A1 Oct. 4, 2007

Related U.S. Application Data

(60) Provisional application No. 60/781,245, filed on Mar. 10, 2006.

(51) Int. Cl.
*C07D 491/00* (2006.01)
*C07D 513/00* (2006.01)
*C07D 487/00* (2006.01)

(52) U.S. Cl. .................. 540/520; 540/579

(58) Field of Classification Search .......... 540/593; 514/213.01
See application file for complete search history.

(56) References Cited

U.S. PATENT DOCUMENTS

| | | | |
|---|---|---|---|
| 3,935,191 A * | 1/1976 | Wendt et al. | ........... 540/585 |
| 5,227,385 A | 7/1993 | Caldwell et al. | |
| 5,262,428 A | 11/1993 | Davies et al. | |
| 5,288,872 A | 2/1994 | Davies et al. | |
| 5,342,949 A | 8/1994 | Davies et al. | |
| 5,591,854 A | 1/1997 | Davies | |
| 5,760,055 A | 6/1998 | Davies | |
| 5,763,455 A | 6/1998 | Davies et al. | |
| 6,008,227 A | 12/1999 | Davies et al. | |
| 6,013,242 A | 1/2000 | Davies et al. | |

OTHER PUBLICATIONS

Michelhaugh et al., Journal of Neurochemistry (2001), 79(5), 1033-1038.*
Davies et al., Journal of Organic Chemistry (2001), 66(23), 7898-7902.*
Becker et al., Tetrahedron Letters (1982), 23(18), 1883-6.*
Bastable et al., Journal of the Chemical Society, Perkin Transactions 1: Organic and Bio-Organic Chemistry (1972-1999) (1981), (5), 1339-45.*
Davies et al., Synthesis of methylphenidate analogues and their binding affinities at dopamine and serotonin transport sites. Bioorganic & Medicinal Chemistry Letters 14 (2004), pp. 1799-1802.

* cited by examiner

*Primary Examiner*—D. Margaret Seaman
*Assistant Examiner*—Niloofar Rahmani
(74) *Attorney, Agent, or Firm*—Hodgson Russ LLP

(57) ABSTRACT

Disclosed are novel homotropane compounds with CNS activity. These compounds can be used for alleviating symptoms of CNS disorders.

16 Claims, No Drawings

HOMOTROPANES WITH CENTRAL NERVOUS SYSTEM ACTIVITY

This application claims priority to U.S. Patent Application Ser. No. 60/781,245, filed on Mar. 10, 2006, the entire disclosure of which is incorporated herein by reference.

This work was supported by Grant Nos. NO1 DA-18826 and 5R01DA15225-03 from the National Institutes of Health. The Government has certain rights in the invention.

FIELD OF THE INVENTION

The present invention relates generally disorders of the central nervous system and more particularly to alleviating symptoms of CNS disorders.

BACKGROUND OF THE INVENTION

Central Nervous System disorders are economically and socially devastating. For example, schizophrenia is one of the leading causes of disability worldwide with a lifetime prevalence of 0.6 to 1.3% characterized by high morbidity and mortality. Only less than 15% of people with this disability are competitively employed, whilst about 20% live independently.

Schizophrenia is generally characterized by positive symptoms (such as delusions, hallucinations, disorganized behavior), negative symptoms (such as anergia), affective symptoms (such as dysphoria, hopelessness, anxiety, hostility, aggression) and/or cognitive deficits.

Typical treatment for such disorders includes drugs that affect the monanine receptor systems. For example, the primary effect of first generation antipsychotics is dopamine (D2 receptor) blockade. While these are effective in treating the positive symptoms of schizophrenia, they exert modest effects on negative symptoms and cognitive deficits. Thus, despite the availability of some drugs for treating central nervous system disorders such as schizophrenia, there are many unmet needs for improved methods and compounds for treating central nervous system disorders.

SUMMARY OF THE INVENTION

Provided are novel homotropanes. The compounds of the present invention are of the following forms

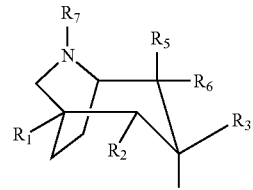
A

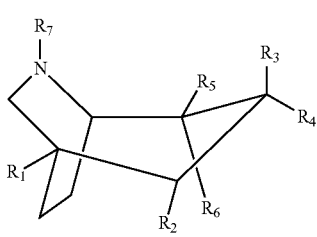
B

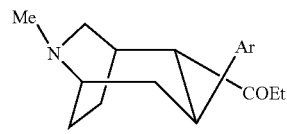
C

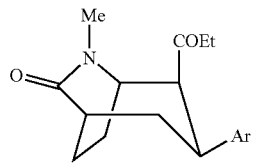
D and their enantiomers, and racemic mixtures; where R1 and R2 are hydrogen, alkanes of 5 carbons or less, or phenyl; R7 is hydrogen or alkane groups of 5 carbons or less; R3 and R4 are hydrogen, substituted or unsubstituted phenyl, or alkane groups of 5 carbons or less, such that one and only one of R3 and R4 is substituted or unsubstituted phenyl; R5 and R6 are hydrogen, alkyl ketone of 5 carbons or less, or alkane groups of 5 carbons or less, such that one and only one of R5 and R6 is alkyl ketone.

Also provided is a method for using the homotropanes to alleviate symptoms of CNS disorders. The method comprises administering to the individual a homotropane in an amount effective to reduce the symptoms of the CNS disorder. Such disease include but are not limited to broad spectrum psychosis such bipolar disorders, depression, mood disorders, addictions, cognitive disorders, and neurodegenerative diseases such as Alzheimer's disease, Parkinson's disease.

DESCRIPTION OF THE INVENTION

The present invention provides novel homotropanes which can function as monoamine transporter inhibitors. Monoamine transporter inhibitors can function as monoamine transporter inhibitors, which have been shown to have significant therapeutic utility in humans. For example, selective serotonin transporter (SERT) inhibitors are some of the most widely used antidepressants. Non selective ligands which bind to SERT as well as to the norepinephrine transporter (NET) have also been launched as antidepressant agents. Dopamine transporter (DAT) inhibitors are used for the treatment of Attention Deficit Disorders (although DAT inhibitors, such as cocaine, can have abuse potential). Thus, monoamine transporter inhibiters have recognized effects in humans. Characterization of the presently provided homotropanes is presented in the Examples.

The compounds of the present invention are of the following forms

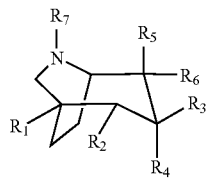
A

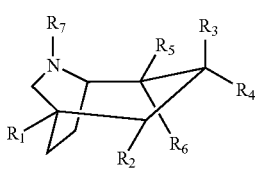
B

C

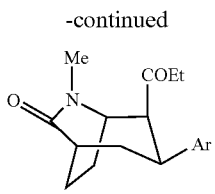

and their enantiomers, and racemic mixtures; where R1 and R2 are hydrogen, alkanes of 5 carbons or less, or phenyl; R7 is hydrogen or alkane groups of 5 carbons or less; R3 and R4 are hydrogen, substituted or unsubstituted phenyl, or alkane groups of 5 carbons or less, such that one and only one of R3 and R4 is substituted or unsubstituted phenyl; R5 and R6 are hydrogen, alkyl ketone of 5 carbons or less, or alkane groups of 5 carbons or less, such that one and only one of R5 and R6 is alkyl ketone.

It is preferred that R1 and R2 be hydrogen, methyl or phenyl; that R3 and R4 be hydrogen and Ar or Ar and hydrogen, respectively.

Ar can be a substituted or unsubstituted phenyl.

With respect to substituted or unsubstituted phenyl groups as referred to herein, ring substituents, if present, can be present as mono-, di- and tri-susbstitutions in which the substituents can be alkyl, alkenyl, alkoxy, halo, nitro, cyano, keto, amino, carboxylate, etc. or a combination thereof. While Ar can generally be substituted or unsubstituted phenyl, Ar is preferably p-tolyl, 2-napthyl, 4-i-PrPh, 4-ClPh, 4-($C_6H_4$)CH=$CH_2$, or 4-($C_6H_4$)C(Me)=$CH_2$; R5 and R6 are preferably hydrogen and alkyl ketone or alkyl ketone and hydrogen, respectively, where the alkyl ketone group is COEt; and R7 is preferably methyl or hydrogen.

In different embodiments, the compound has the structure of structure A, wherein:
R1, R2, R4 and R6 are hydrogen, R3 is p-tolyl, R5 is —COEt, and R7 is methyl;
R1, R2 and R4 and R6 are hydrogen, R3 is 2-napthyl, R4 is hydrogen, R5 is —COEt, and R7 is methyl;
R1, R2, R4 and R6 are hydrogen, R3 is 4-i-PrPh, R5 is —COEt, and R7 is methyl;
R1, R2, R4 and R6 are hydrogen, R3 is 4-ClPh, R5 is —COEt, and R7 is methyl;
R1, R2, R4 and R6 are hydrogen, R3 is 4-($C_6H_4$)CH=$CH_2$, R5 is —COEt, and R7 is methyl;
R1, R2, R4 and R6 are hydrogen, R3 is 4-($C_6H_4$)C(Me)=$CH_2$, R5 is —COEt, and R7 is methyl
R1 is hydrogen, R2 is methyl, R4 and R6 are hydrogen, R3 is p-tolyl, R5 is —COEt, R7 is methyl;
R1 is hydrogen, R2 is phenyl, R4 and R6 are hydrogen, R3 is p-tolyl, R5 is —COEt, R7 is methyl;
R1, R2 and R7 are methyl, R3 is p-tolyl, R4 and R6 are hydrogen, R5 is —COEt;
R1 and R7 are methyl, R2 is phenyl, R3 is p-tolyl, R4 is hydrogen, R5 is —COEt, R6 is hydrogen;
R1 and R7 are methyl, R2 is phenyl, R3 is p-tolyl, R4 is hydrogen, R5 is —COEt, R6 is hydrogen;
R1, R2, R4 and R5 are hydrogen, R3 is p-tolyl, R6 is —COEt, R7 is methyl;
R1, R2, R4 and R5 are hydrogen, R3 is 2-naphthyl, R6 is —COEt, R7 is methyl;
R1, R2, R4, R6 and R7 are hydrogen, R3 is p-tolyl, R5 is —COEt.

In other embodiments, the compound has the structure of structure B, wherein
R1, R2, R3, R6 and R7 are hydrogen, R4 is p-tolyl, R5 is —COEt R1, R2, R3, R6 and R7 are hydrogen, R4 is 4-($C_6H_4$)C(Me)=$CH_2$, R5 is —COEt or the compound has the structure C or D, wherein Ar is a p-tolyl group.

In another embodiment, the present invention provides a method for alleviating symptoms of CNS disorders. The method comprises administering to an individual a composition comprising homotropanes in an amount effective to reduce the symptoms of the CNS disorder.

The method of the invention is suitable for alleviating one or more symptoms of a variety of CNS disorders. Individuals with a CNS disorder frequently exhibit one or more symptoms that are characteristic of the particular disorder. It is also contemplated that a constellation of symptoms from multiple CNS disorders in the same individual can be alleviated by the present method. In this regard, recognizing symptoms from CNS disorders, and determining alleviation of said symptoms during or after practice of the present method is well within the purview of a person having ordinary skill in the art and can be performed using any suitable clinical, diagnostic, observational or other techniques. For example, symptoms of schizophrenia include but are not limited to delusions, hallucinations and catatonic behavior. A reduction in any of these particular symptoms resulting from practicing the method of the invention is considered an alleviation of the symptom. Particular CNS disorders presenting symptoms suitable for alleviation by the present method include but are not limited to: broad spectrum psychosis such as bipolar disorders, depression, mood disorders, drug addictions, cognitive disorders, neurodegenerative disorders such as Alzheimer's disease and Parkinson's disease, and combinations thereof. Symptoms of each of these disorders are well known. Recognizing and determining a reduction in the symptoms of any of these particular disorders can be readily performed by those skilled in the art.

Compositions comprising an effective amount of the compound may be administered via any conventional route. Such routes include but are not limited to orally, parenterally, intramuscularly, intravenously and mucosally. In one embodiment, the route of administration is oral. Determining a dosage regimen of the compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg. It will be recognized by that dosing parameters, in addition to the weight of the individual, also take into account the age of the individual and the stage of the disease and can be determined according to conventional procedures Other components may be combined with the compounds to form pharmaceutical preparations for use in the present method. Such components can be selected depending on factors which include but are not limited to the dosage form, particular needs of the patient, and method of manufacture, among other things. Examples of such components include but are not limited to binders, lubricants, fillers, flavorings, preservatives, colorings, diluents, etc. Additional information regarding pharmaceutical composition components for use with the present method are described in Remington's Pharmaceutical Sciences (18th Edition, A. R. Gennaro et al. Eds., Mack Publishing Co., Easton, Pa., 1990). Accordingly, the selection of particular substances and their compatibilities with the compositions of the present invention can be readily ascertained by those of ordinary skill in the art. Additional details are provided in U.S. Pat. No. 5,763,455, which is incorporated herein by reference.

While the present invention is illustrated by way of the following examples, the examples are meant only to illustrate particular embodiments of the present invention and are not meant to be limiting in any way.

EXAMPLE 1

Long acting DAT inhibitors have been explored as potential medications for the treatment of cocaine (1) addiction. The most widely studied systems has been the 3β-aryl-2β-carboxylates (2), several of which are up to 500 times more potent than cocaine at binding to DAT.

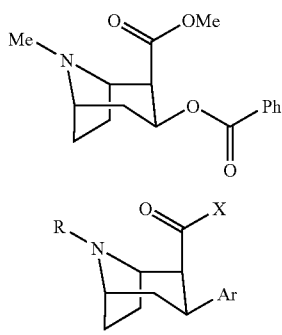

While many of the first generation tropane analogs were synthesized using cocaine as the starting material, this approach limits the structural diversity that can be obtained in the final compounds. We have exploited a flexible synthetic route to the tropane ring system via the [3+4] cycloaddition between rhodium-stabilized vinylcarbenoids with pyrroles (eq 1). Not only can a diverse range of substitution patterns be accommodated, enantiomerically pure tropanes, including the biologically relevant aryltropanes 3, can be synthesized on multigram scale. The majority of the tropanes that have been prepared by this scheme have an acyl functionality at C-2, which is expected to enhance metabolic stability. The most notable tropanes that have been developed to date are: the tolyl derivative 3a, which has been extensively evaluated as a potential medication for cocaine addiction, the naphthyl derivative 3b, which is one of the most potent 3β-aryl tropanes known, the isopropyl derivative 3c, which is one of the first reported SERT selective tropanes, the normethyl derivative 3d which has enhanced SERT selectivity, and the isopropenyl derivative 3e which has very high affinity for SERT.

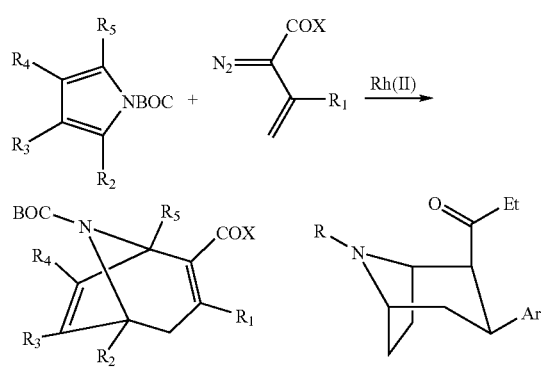

3a: Ar = p-tolyl, R = Me
3b: Ar = 2-naphthyl, R = Me
3c: Ar = 4-i-PrPh, R = Me
3d: Ar = p-tolyl, R = H
3e: Ar = —(C$_6$H$_4$)C(Me)=CH$_2$, R = H It was envisioned that novel biological activity complimentary to tropanes could be obtained from the 6-azabicylo[3.2.2]nonane system. This system had not been studied previously because their accessibility would be difficult using conventional chemistry. We have developed new chemistry to solve this synthesis problem. The synthesis of both regioisomeric 6-azabicyclo[3.2.2]nonanes 4 and 5 were achieved via the rhodium(II)-catalyzed decomposition of vinyldiazoacetates in the presence of suitably protected 1,2-dihydropyridines (eq 2). In addition, preparation of the 6-azabicyclo[3.2.2]nona-7-one ring system 6 has been achieved in moderate yield from the reaction between vinylcarbenoids and 1-methyl-2-pyridone (eq 3). The synthesis has now been extended to the reparation of biologically active 6-azabicyclononane derivatives.

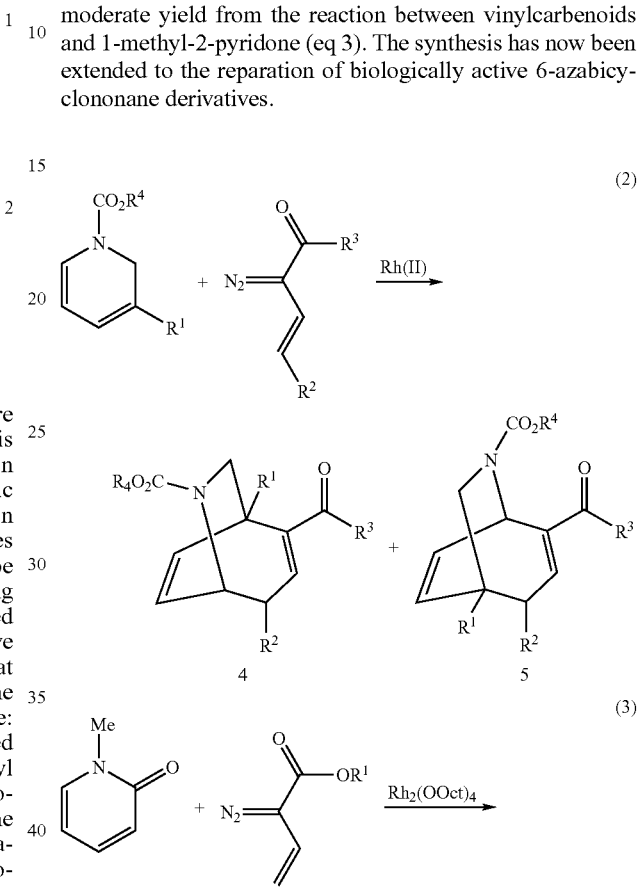

The 6-azabicyclo[3.2.2]nonadienes were synthesized by the general synthetic schemes shown in eqs 2 and 3. A series of 3β, 4β analogs 12 were prepared from either the ethyl ketone 7 or the ester 8 (Scheme 1). As reported for the tropane system, the final 6-azabicyclo[3.2.2]nonanes were synthesized by employing a copper catalyzed 1,4-addition to the corresponding α,β-unsaturated derivative 11, followed by a low temperature quench with anhydrous HCl. The N-methyl-4-substituted azabicyclo[3.2.2]nonenes (11), which have the bridgehead nitrogen closest to the carbonyl group, gave moderate to good yields of the desired 3β, 4β isomers 12 with little to none of the trans-(3β, 4α) isomer 13. Alternatively, by quenching the reaction at room temperature, significant amounts of the trans-(3β, 4α) isomers 13 can be obtained.

Scheme 1

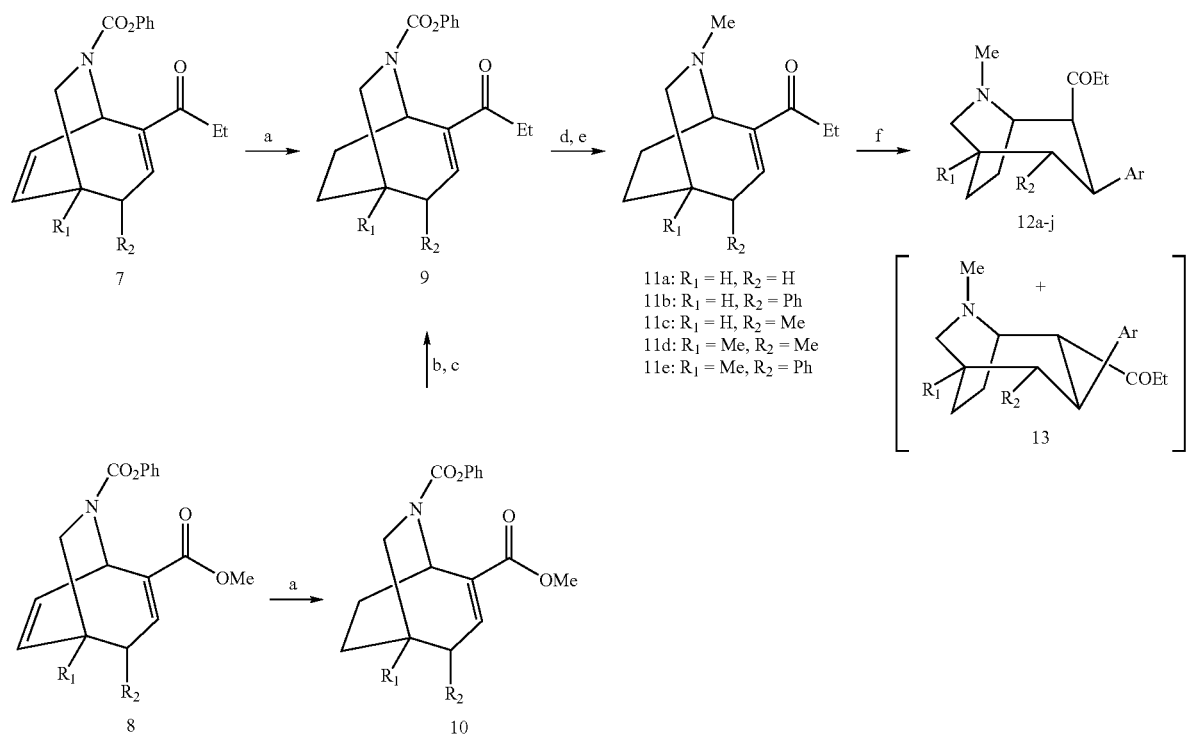

(a) H₂, (PPh₃)₃RhCl; (b) NH(Me)OMe·HCl, i-PrMgCl (2 equiv); (c) EtMgBr; (d) LAH, D; (e) Swern or Dess-Martin; (f) 1. ArMgBr, Cu(I) 2. HCl/Et₂O, -78Þ C.

The normethyl derivatives 18 and 19 were prepared from the 2,2,2-trichloroethoxycarbonyl (TROC)-protected azabicyclononandiene 14 (Scheme 2). The precursor 16 was prepared first by hydrogenation of 14 to 15 followed by removal of the protecting group under standard conditions. Cuprate addition to 16 failed to give the expected 3β, 4β analog 19. Instead the aryl cuprate approached from the endo face of 16 to give 18, in which both substituents are axially oriented, followed by a chair-chair equilibration to ultimately place both substituents in an equatorial conformation. The desired 3β, 4β analog 19 could be prepared by first conversion of 16 to the N-benzyl derivative 17 followed by cuprate addition and debenzylation (H₂/Pd/C in EtOH).

Scheme 2

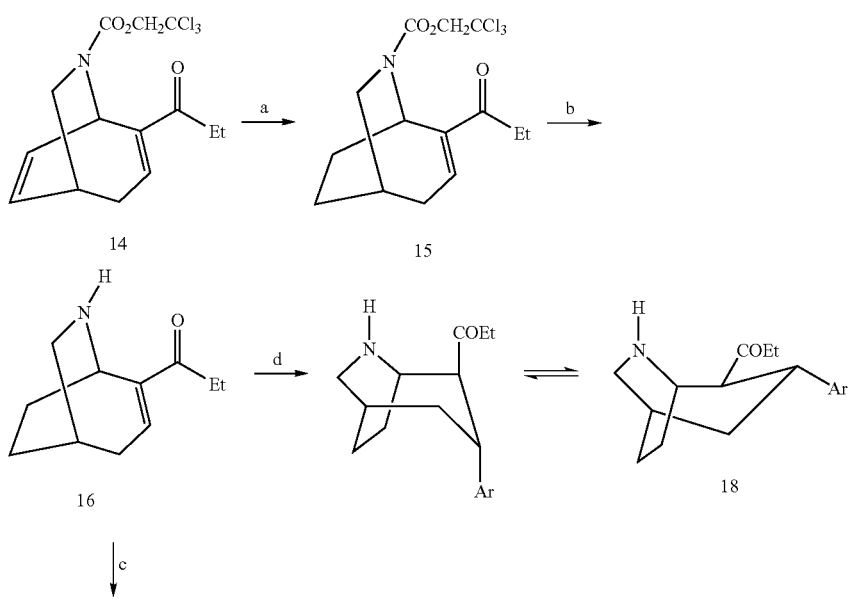

-continued

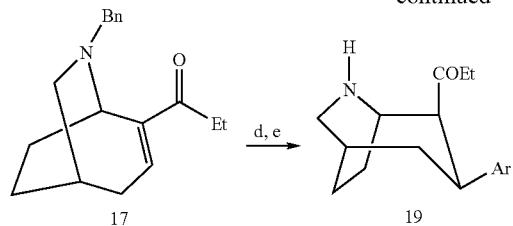

(a) H$_2$, (PPh$_3$)$_3$RhCl; (b) Zn, HOAc; (c) BnBr, i-Pr$_2$EtN; (d) 1. ArMgBr, Cu(I) 2. HCl/Et$_2$O, -78Þ C.; (e) H$_2$, Pd/C, EtOH

The 6-azabicyclononane regioisomer 20 was converted to the corresponding N-methyl derivative 22 using the same sequence as described for the synthesis of 11 from 7 (Scheme 3). The cuprate addition to 22, however, gave only the 3α, 4β isomer 23. A prerequisite for an effective kinetic protonation to form the 3β-isomer is the presence of an appropriately positioned heteroatom on the bicyclic system and this is not the case with compound 18.[11]

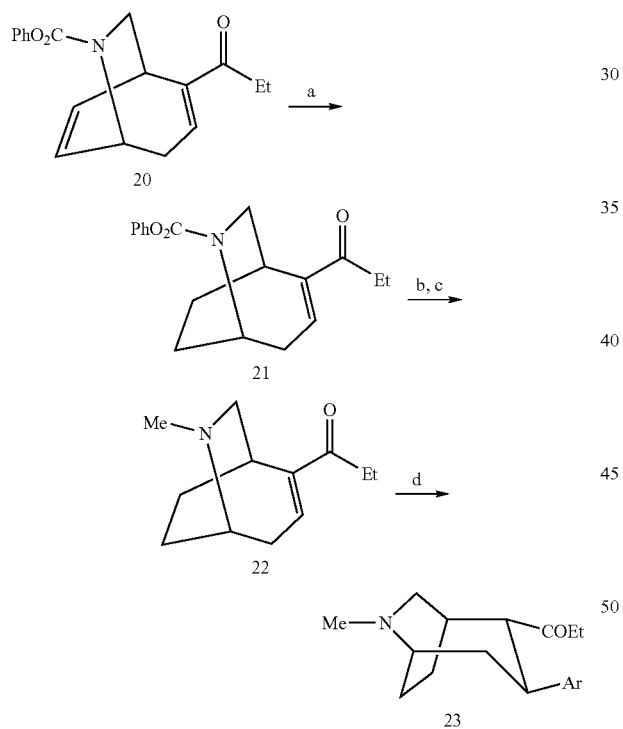

(a) H$_2$, (PPh$_3$)$_3$RhCl; (b) LAH, Δ; (c) Swern or Dess-Martin; (d) 1. ArMgBr, Cu(I) 2. HCl/Et$_2$O, -78Þ C.;

The glycolate-substituted 6-azabicyclononadienone 24 was elaborated using a slightly different methodology. Hydrogenation followed by removal of the glycolate moiety via methanolysis followed by hydrolysis gave the acid 25. Conversion of 25 to the acid chloride followed by nucleophilic displacement gave the ethyl ketone derivative 26. The cuprate induced conjugate addition to 26 generated the 3β, 4β isomer 27.

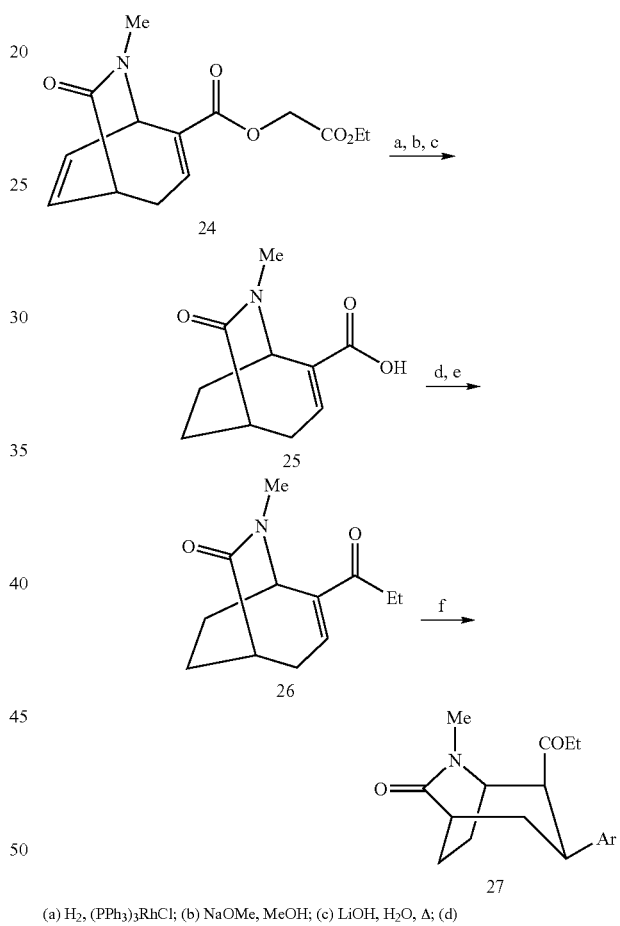

(a) H$_2$, (PPh$_3$)$_3$RhCl; (b) NaOMe, MeOH; (c) LiOH, H$_2$O, Δ; (d) SOCl$_2$; (e) EtMgBr, Cu(I); (f) 1. ArMgBr, Cu(I) 2. HCl/Et$_2$O, -78Þ C.;

Experimental Procedures Compounds 7, 8, 14, 20 and 24 were prepared as previously described. The compounds that contain either the phenoxycarbonyl or 2,2,2-trichloroethoxycarbonyl group on the nitrogen contain rotamers; the $^1$H NMR resonances corresponding to the major rotamer are underlined.

EXAMPLE 2

4-Propionyl-(6-phenoxycarbonyl-6-azabicylo[3.2.2]non-3-ene) [9aa] Typical Procedure. A solution of 7a (6.9 g, 23 mmol) in 150 mL absolute ethanol was prepared and transferred to a Parr™ hydrogenation flask. Wilkinson's catalyst (325 mg, 0.351 mmol) was added, and the flask flushed with $H_2$ (50 psi) four times. The reaction was agitated at 50 psi for 24 h. The solvent was evaporated, and the product chromatographed (2:1 petroleum ether/$Et_2O$) to give the title compound as a light yellow oil. Yield: 6.32 g (21.1 mmol, 91%). $^1H$ NMR (3:2 ratio of rotamers, 500 MHz, $CDCl_3$), δ 7.35-7.29 (m, 2 H), 7.18-7.11 (m, 2 H), 7.04 (d, J=8.1 Hz, 1 H), 6.84, 6.79 (dd, J=4.6, 4.0 Hz, 1 H total), 5.34, 5.25 (br s, 1 H total), 3.89, 3.83 (d, J=12.2 Hz, 1 H total), 3.62, 3.45 (d, J=12.2 Hz, 1 H total), 2.70 (m, 4 H), 2.36 (m, 1 H), 2.19 (m, 1 H), 1.99 (m, 1 H), 1.86 (m, 1 H), 1.67 (m, 1 H), 1.10 (m, 3 H); IR (neat): 3063, 3043, 2974, 2936, 2872, 2816, 1718, 1666, 1642, 1495, 1403 $cm^{-1}$; MS m/e (rel int): 299 ($M^+$, 8), 206 (100). Anal. Calcd for $C_{18}H_{21}NO_3$: C, 72.22; H, 7.07; N, 4.68. Found: C, 72.09; H, 7.03; N, 4.59. Compounds I0b-e, 15, and 17 were prepared by a similar procedure; the yield and characterization data are presented for these compounds.

EXAMPLE 3

Methyl(2α-phenyl-6-phenoxycarbonyl-6-azabicyclo[3.2.2]nona-3-ene)-4-carboxylate [10b][10] (97%). Mp=98.5-100° C. $^1H$ NMR (400 MHz, $CDCl_3$, 3:2 ratio of rotamers) δ 7.39-7.10 (m, 11 H), 5.38, 5.35 (br s, 1 H total), 4.05, 3.99 (ddd, J=12.4, 2, 2 Hz, 1 H total), 4.04 (br s, 1 H), 3.80, 3.61 (dd, J=12.4, 3.3 Hz, 1 H total), 3.79, 3.78 (s, 3 H total), 2.33 (m, 1 H), 2.19 (m, 1 H), 2.07 (m, 1 H), 1.81 (m, 1 H), 1.56 (m, 1 H); IR (neat): 3059, 3026, 2949, 2929, 2872, 1715, 1494, 1405, 1206 $cm^{-1}$; MS m/e (rel int): 377 ($M^+$, 8), 284 (100). Anal. Calcd for $C_{23}H_{23}NO_4$: C, 73.19; H, 6.14; N, 3.71. Found: C, 73.23; H, 6.17; N, 3.76.

EXAMPLE 4

Methyl(2α-methyl-6-phenoxycarbonyl-6-azabicyclo[3.2.2]nona-3-ene)-4-carboxylate [10c] (100%). $^1H$ NMR (3:2 ratio of rotamers, 400 MHz, $CDCl_3$) δ 7.33 (m, 2 H), 7.14 (m, 3 H), 6.78 (br s, 1 H), 5.22, 5.18 (br t, 1 H total), 3.89, 3.82 (br d, J=12.1 Hz, 1 H total), 3.75, 3.74 (s, 3 H total), 3.65, 3.47 (dd, J=12.9, 2.9 Hz, 1 H total), 2.84 (m, 1 H), 2.13 (m, 1 H), 1.98 (m, 2 H), 1.86-1.64 (m, 2 H), 1.22, 1.21 (d, J=7.3 Hz, 3 H total); IR (neat) 3063 (w), 3042 (w), 2951, 2872, 1716, 1645, 1593, 1435, 1404 $cm^{-1}$; MS m/e (rel int), 315 ($M^+$, 9), 222 (100). Anal. Calcd for $C_{18}H_{21}NO_4$: C, 68.55; H, 6.71; N, 4.44. Found: C, 68.28; H, 6.81; N, 4.34.

EXAMPLE 5

Methyl (1,2α-dimethyl-6-phenoxycarbonyl-6-azabicyclo[3.2.2]nona-3-ene)-4-carboxylate [10d] (93%). $^1H$ NMR (500 MHz, $CDCl_3$, 3:2 ratio of rotamers) δ 7.33 (m, 2 H), 7.17 (t, J=7.6 Hz, 1 H), 7.11, 7.08 (d, J=7.6 Hz, 2 H total), 6.79, 6.77 (d, J=3.1 Hz, 1 H total), 5.27, 5.21 (d, J=5.2 Hz, 1 H total), 3.75, 3.74 (s, 3 H total), 3.63, 3.56 (br d, J=12.2 Hz, 1 H total), 3.49, 3.33 (d, J=12.2 Hz, 1 H total), 2.55 (m, 1 H), 2.15 (m, 1 H), 1.88 (m, 2 H), 1.36 (m, 1 H), 1.16, 1.14 (d, J=7.3 Hz, 3 H total), 1.01, 0.99 (s, 3 H total); IR (neat): 3065, 3043, 2950, 2873, 1716 (broad), 1650, 1594, 1495, 1407 $cm^{-1}$; MS m/e (rel int): (329 $M^+$, 9), 236 (100). Anal. Calcd. for $C_{19}H_{23}NO_4$: C, 69.28; H, 7.04; N, 4.25. Found: C, 69.32; H, 7.07; N, 4.21.

EXAMPLE 6

Methyl (1-methyl-2α-phenyl-6-phenoxycarbonyl-6-azabicyclo[3.2.2]nona-3-ene)-4-carboxylate [10e] (96%). $^1H$ NMR (400 MHz, $CDCl_3$, 3:2 ratio of rotamers) δ 7.24 (m, 4 H), 7.16 (m, 6 H), 6.96, 6.94 (d, J=2.6 Hz, 1 H total), 5.43, 5.40 (d, J=5.1 Hz, 1 H total), 3.75 (s, 3 H), 3.79, 3.69 (dd, J=12, 2 Hz, 1 H total), 3.7 (br s, 1 H), 3.61, 3.43 (d, J=12.8 Hz, 1 H total), 2.23 (m, 1 H), 2.05 (m, 2 H), 1.33 (m, 1 H), 0.81, 0.79 (s, 3 H total); IR (neat): 3096, 3060, 3043, 2933, 2870, 2821, 1716 (broad), 1663 (broad), 1593, 1495, 1404, 1304, 1205, 1114, 1074, 1029, 969, 879, 859, 754, 691; MS m/e (rel int): 391 ($M^+$, 9), 298 (100), 266 (52), 91 (53). Anal. Calcd. for $C_{24}H_{25}NO_4$: C, 73.64; H, 6.44; N, 3.58. Found: C, 73.53; H, 6.50; N, 3.53.

EXAMPLE 7

2α-Phenyl-4-propionyl-(6-phenoxycarbonyl)-6-azabicylo[3.2.2]non-3-ene [9b] Typical Procedure. A solution of 10b (4.2 g, 11 mmol) in 100 mL dry THF was prepared, and N,O-dimethylhydroxylamine hydrochloride (1.63 g, 16.7 mmol) was added. The mixture was cooled to −15° C. in an ice-salt bath, and a solution of i-PrMgCl (Aldrich, 2.0 M in THF, 17 mL, 34 mmol) was added dropwise over ~5 min. The reaction was stirred for 3 h and quenched at 0° C. with 100 mL sat aq $NH_4Cl$. Diethyl ether (150 mL) was then added and the layers separated. The aqueous layer was washed with 75 mL $Et_2O$, and the organic layers combined, back-extracted with 100 mL brine, dried ($MgSO_4$), and evaporated to give the crude amide, which was used in the next step without purification.

All of the above material was dissolved in 100 mL dry THF and cooled to 0° C. A solution of EtMgBr (Aldrich, 3.0 M, 6.0 mL, 18 mmol) was added, and the reaction stirred for 3 h. The reaction was quenched with 125 mL of sat aq $NH_4Cl$. Diethyl ether (100 mL) was then added, and the layers separated. The aqueous layer was extracted with 75 mL $Et_2O$, and the organic extracts were combined, back-extracted with 100 mL brine, dried ($MgSO_4$), and evaporated to give the crude product. The crude mixture was chromatographed (4:1-1:1 petroleum ether/$Et_2O$) to give the title compound along with a trace amount of the starting amide. Yield: 2.84 g (7.57 mmol, 69% overall). $^1H$ NMR (400 MHz, $CDCl_3$, 2:1 ratio of rotamers) δ 7.41-7.07 (m, 10 H), 6.93, 6.89 (br s, 1 H total), 5.47, 5.38 (br s, 1 H total), 4.12 (br s, 2 H), 4.07, 4.00 (br d, J=12.0 Hz, 1 H total), 3.78, 3.59 (dd, J=12.0, 3.3 Hz, 1 H total), 2.90-2.60 (m, 2 H), 2.33 (m, 1 H), 2.19 (m, 1 H), 1.99 (m, 1 H), 1.79 (m, 1 H), 1.14, 1.11 (t, J=7.3 Hz, 3 H); IR (neat): 3059, 3043, 3026, 2936, 2782, 1715, 1669, 1593, 1494, 1455, 1206 $cm^{-1}$; MS m/e (rel int): 375 ($M^+$, 6), 282 (100). Anal. Calcd for $C_{24}H_{25}NO_3$: C, 76.78; H, 6.71; N, 3.73. Found: C, 76.52; H, 6.89; N, 3.64.

Compounds 9c-e were synthesized from compounds 10c-e using a similar procedure; yields and characterization data are provided for these compounds.

EXAMPLE 8

2α-Methyl-4-propionyl-(6-phenoxycarbonyl)-6-azabicylo[3.2.2]non-3-ene [9c] (73% overall from 10c). $^1H$ NMR (400 MHz, $CDCl_3$, 2:1 rotamer ratio) δ 7.32 (m, 2 H), 7.14 (m, 1 H), 7.03 (d, J=7.7 Hz, 2 H), 6.57, 6.54 (br s, 1 H total), 5.31, 5.21 (br t, 1 H total), 3.89, 3.83 (br d, J=12.1 Hz, 1 H total), 3.63, 3.46 (dd, J=12.5, 2.9 Hz, 1 H total), 2.90 (m, 1 H), 2.80-2.57 (m, 2 H), 2.17 (m, 1 H), 2.01 (m, 1 H), 1.88 (m, 1 H), 1.74 (m, 2 H), 1.23 (d, J=7.7 Hz, 3 H), 1.10, 1.07 (t, J=7.3 Hz, 3 H total); IR (neat): 3043, 2960, 2936, 2873, 1716, 1668, 1638, 1593, 1495, 1456, 1403 $cm^{-1}$; MS m/e (rel int): 313 ($M^+$, 6), 220 (100). Anal. Calcd for $C_{19}H_{23}NO_3$: C, 72.82; H, 7.40; N, 4.47. Found: C, 72.55; H, 7.45; N, 4.42.

EXAMPLE 9

1,2α-Dimethyl-4-propionyl-(6-phenoxycarbonyl)-6-azabicylo[3.2.2]non-3-ene [9d] (76% overall from 10d). $^1$H NMR (500 MHz, CDCl$_3$, 2:1 rotamer ratio), δ 7.31 (m, 2 H), 7.13 (m, 2 H), 7.05 (d, J=7.6 Hz, 1 H), 6.59, 6.55 (d, J=2.7 Hz, 1 H), 5.36, 5.24 (d, J=3.7 Hz, 1 H), 3.65, 3.57 (d, J=12.5 Hz, 1 H), 3.47, 3.32 (d, J=12.8 Hz, 1 H), 2.81-2.58 (m, 3 H), 2.16 (m, 1 H), 1.81 (m, 2 H), 1.34 (dd, J=11.6, 11.9 Hz, 1 H), 1.16 (d, J=7.3 Hz, 3 H), 1.10, 1.07 (t, J=7.3 Hz, 3H total), 1.01, 1.00 (s, 3 H total); IR (neat): 3065, 3042, 2969, 2936, 2874, 1716 (broad), 1668, 1644, 1594, 1495, 1456, 1404, 1207 cm$^{-1}$; MS m/e (rel int): 327 (M$^+$, 5), 234 (100). Anal. Calcd for C$_{20}$H$_{25}$NO$_3$: C, 73.37; H, 7.70; N, 4.28. Found: C, 73.29; H, 7.80; N, 4.17.

EXAMPLE 10

1-Methyl-2α-phenyl-4-propionyl-(6-phenoxycarbonyl)-6-azabicylo[3.2.2]non-3-ene [9e] (75% overall from 10e). $^1$H NMR (400 MHz, CDCl$_3$, 2:1 rotamer ratio) δ 7.34 (m, 5 H), 7.17 (m, 4 H), 7.08 (d, J=7.7 Hz, 1 H), 6.77, 6.73 (d, J=2.6 Hz, 1 H total), 5.51, 5.43 (d, J=5.1 Hz, 1 H total), 3.80, 3.74 (br d, J=12.1 Hz, 1 H), 3.76 (br s, 1 H), 3.59, 3.42 (d, J=12.5 Hz, 1 H total), 2.80-2.58 (m, 2 H), 2.23 (m, 1 H), 2.00 (m, 2 H), 1.31 (m, 1 H), 1.10 (m, 3 H), 0.80, 0.78 (s, 3 H total); IR (KBr): 3026, 2973, 2957, 2936, 2869, 1716, 1660, 1595, 1492, 1414 cm$^{-1}$; MS m/e (rel int): 389 (M$^+$, 4), 296 (100). Anal. Calcd for C$_{25}$H$_{27}$NO$_3$: C, 77.09; H, 6.99; N, 3.60. Found: C, 77.01; H, 7.04; N, 3.57.

EXAMPLE 11

4-Propionyl-6-methyl-6-azabicylo[3.2.2]non-3-ene [11a] A solution of 9a (5.07 g, 16.9 mmol) was prepared in 150 mL dry THF, and LAH (3.85 g, 101 mmol, 6 equiv) was added in portions with stirring under argon. The reaction was heated to reflux for 1 h and allowed to cool to rt. The mixture was then cooled to 0° C., and the reaction quenched by slow addition of EtOAc (100 mL) followed by water (50 mL). The mixture was diluted with 200 mL each of water and EtOAc and filtered through Celite. The layers were separated, and the aqueous layer washed with EtOAc (2×100 mL). The organic washings were combined and extracted with 10% HCl (3×100 mL). The aqueous extracts were then combined, neutralized with NaHCO$_3$ (s) and basified to pH 11-12 with NH$_4$OH. The solution was extracted with CH$_2$Cl$_2$ (4×100 mL) and the organic extracts dried (MgSO$_4$) and evaporated to give a light tan oil, which was shown by $^1$H NMR to be a 1:1 mixture of the diastereomeric alcohols. Yield: 3.35 g, 100%.

EXAMPLE 12

Oxidation Swern (Method A): A solution of freshly distilled oxalyl chloride (1.8 mL, 21 mmol) in 25 mL dry CH$_2$Cl$_2$ was prepared and cooled to −78° C. A solution of dry DMSO (3.0 mL, 42 mmol) in 5 mL CH$_2$Cl$_2$ was added via a pressure-equalized dropping funnel over 2-3 min giving gas evolution. A solution of the crude alcohol (3.08 g, 15.8 mmol) in 30 mL CH$_2$Cl$_2$ was added dropwise over 5 min. The mixture was stirred for 15 min, and Et$_3$N (13 mL, 93 mmol) was added. The reaction was stirred for an additional 5 min at −78° C. and warmed to 0° C. The reaction mixture was added to a mixture of NH$_4$OH (100 mL) and water (50 mL) and the layers separated. The aqueous solution was extracted with CH$_2$Cl$_2$ (2×50 mL) and the organic extracts combined, washed with 100 mL brine, dried (MgSO$_4$), and evaporated to give the crude product as a yellow oily solid. The crude product was chromatographed (10:9:1 pentane/Et$_2$O/Et$_3$N) to give the title compound as a light yellow oil. Yield: 2.01 g (10.4 mmol, 66% overall from 9a). $^1$H NMR (500 MHz, CDCl$_3$), δ 6.95 (br s, 1 H), 3.96 (d, J=5.8 Hz, 1 H), 2.92 (m, 1 H), 2.71 (m, 3 H), 2.53 (m, 2 H), 2.30 (s, 3 H), 2.21 (m, 1 H), 2.11 (br s, 1 H), 1.85 (m, 1 H), 1.61 (m, 2 H), 1.10 (t, J=7.3 Hz, 3 H); $^{13}$C NMR (125 MHz, CDCl$_3$), δ 201.2, 143.5, 142.4, 55.8, 51.9, 43.8, 38.7, 30.1, 28.9, 27.1, 23.9, 8.9; IR (neat): 3035, 2935, 2867, 2788, 1663, 1637 cm$^{-1}$. HRMS calcd for C$_{12}$H$_{19}$NO 193.1467; found 193.1470. Compounds 11b-e were prepared using similar procedures; characterization data is provided for these compounds.

EXAMPLE 13

2α-Phenyl-4-propionyl-6-methyl-6-azabicylo[3.2.2]non-3-ene [11b] (Method A, ~70% overall from 9b). $^1$H NMR (500 MHz, CDCl$_3$ δ 7.35 (t, J=7.6 Hz, 2 H), 7.27 (m, 1 H), 7.19 (d, J=8.0 Hz, 2 H), 7.01 (d, J=4.3 Hz, 1 H), 4.02 (m, 2 H), 3.13 (dd, J=10.7, 5.7 Hz, 1 H), 2.78 (q, J=7.3Hz, 2 H), 2.60 (d, J=11.0 Hz, 1 H), 2.32 (s, 3 H), 2.20 (m, 1 H), 2.12 (m, 1 H), 1.63 (m, 1 H), 1.54 (m, 1 H), 1.43 (m, 1 H), 1.14 (t, J=7.3 Hz, 3 H); $^{13}$C NMR (125 MHz, CDCl$_3$), δ 201.7, 144.6, 143.4, 141.9, 128.6, 127.9, 126.8, 56.4, 54.3, 51.4, 43.9, 36.6, 30.5, 27.5, 18.8, 8.9; IR (neat): 3080, 3059, 3025, 2936, 2864, 2842, 2792, 2768, 1667, 1634, 1601, 1492, 1451 cm$^{-1}$; HRMS calcd for C$_{18}$H$_{23}$NO 269.1780; found 269.1783.

EXAMPLE 14

2α-Methyl-4-propionyl-6-methyl-6-azabicylo[3.2.2]non-3-ene [11c] (Method A, 70% overall from 9c). $^1$H NMR (500 MHz, CDCl$_3$), δ 6.71 (d, J=3.4 Hz, 1 H), 3.86 (d, J=5.8 Hz, 1 H), 2.90 (dd, J=10.7, 5.2 Hz, 1 H), 2.82 (m, 1 H), 2.71 (q, J=7.3 Hz, 2 H), 2.54 (d, J=10.7 Hz, 1 H), 2.28 (s, 3 H), 2.11 (m, 1 H), 1.83 (br s, 1 H), 1.69 (m, 2 H), 1.52 (m, 1 H), 1.15 (d, J=7.3 Hz, 3 H), 1.09 (t, J=7.3 Hz, 3 H); $^{13}$C NMR (125 Hz, CDCl$_3$), δ 201.6, 147.1, 142.7, 56.7, 51.8, 44.0, 42.1, 34.8, 30.1, 26.5, 18.9, 18.8, 8.9. IR (neat): 3030 (weak), 2959, 2935, 2900, 2871, 2842, 2790, 2767, 1667, 1634, 1458, 1442 cm$^{-1}$. HRMS calcd for C$_{13}$H$_{21}$NO 207.1623; found 207.1628. Note: This compound readily decomposes upon standing at room temperature or during repeated or prolonged column chromatography.

EXAMPLE 15

1,2α-Dimethyl-4-propionyl-6-methyl-6-azabicylo[3.2.2]non-3-ene [11d] (Method B (vide infra), 26% overall from 9d). $^1$H NMR (500 MHz, CDCl$_3$), δ 6.78 (dd, J=5.5, 1.2 Hz, 1 H), 3.98 (d, J=7.9 Hz, 1 H), 2.77 (d, J=11.0 Hz, 1 H), 2.76-2.66 (m, 3 H), 2.32 (m, 2 H), 2.17 (s, 3 H), 2.16 (m, 1 H), 1.70 (m, 1 H), 1.55 (m, 1 H), 1.45 (m, 1 H), 1.103 (t, J=7.3 Hz, 3 H), 1.100 (d, J=7.3 Hz, 3 H), 0.93 (s, 3 H); $^{13}$C NMR (125 Hz, CDCl$_3$), δ 201.9, 147.3, 139.6, 63.5, 50.3, 47.6, 43.1, 34.9, 30.0, 28.3, 28.0, 26.6, 14.7, 9.0; IR (neat): 2961, 2936, 2873, 2787, 1668, 1637 cm$^{-1}$; HRMS calcd for C$_{14}$H$_{23}$NO 221.1780; found 220.1781.

EXAMPLE 16

1-Methyl-2α-phenyl-4-propionyl-6-methyl-6-azabicylo[3.2.2]non-3-ene [11e] (Method A, 72% overall from 9e). $^1$H NMR (500 MHz, CDCl$_3$), δ 7.32 (m, 3 H), 7.19 (m, 2 H), 6.86 (dd, J=4.6, 0.9 Hz, 1 H), 4.09 (d, J=7.3 Hz, 1 H), 3.55 (J=4.6, 1.2 Hz, 1 H), 2.93 (d, J=11.0 Hz, 1 H), 2.70 (m, 2 H), 2.34 (dd, J=11.0, 1.8 Hz, 1 H), 2.26 (s, 3 H), 2.18 (m, 1 H), 1.77 (m, 1 H), 1.45 (m, 2 H), 1.10 (t, J=7.3 Hz, 3 H), 0.86 (s, 3 H); $^{13}$C NMR (75 MHz, CDCl$_3$), δ 202.1, 143.9, 141.9, 139.2, 130.0, 128.2, 127.2, 63.7, 61.0, 50.3, 43.5, 36.2, 30.3, 28.9, 28.1, 26.6, 8.9; IR (neat): 3082, 3059, 3027, 2951, 2935, 2871, 2842, 2787, 2765, 1669, 1634, 1599, 1493, 1457 cm$^{-1}$; HRMS calcd for C$_{19}$H$_{25}$NO 283.1936; found 283.1946.

EXAMPLE 17

4-Propionyl-6-(2,2,2-trichloroethoxycarbonyl)-6-azabicyclo[3.2.2]nona-3,8-diene [14] A solution of freshly purified 4-diazo-5-hexen-2-one (13.8 g, 111 mmol) in 140 mL dry hexanes was added to a solution of N-(2,2,2-trichloroethoxycarbonyl)-1,2-dihydropyridine (32.2 g, 126 mmol) and Rh$_2$(OPiv)$_4$ (1.38 g, 2.26 mmol) in 100 mL dry hexanes. The mixture was stirred at room temperature for 30 min then heated to reflux for 30 min. The mixture was cooled to room temperature and the solvent removed under reduced pressure. The mixture was chromatographed (9:1 to 1:1 petroleum ether/Et$_2$O) to give the title compound as a light yellow oil. Yield: 6.61 g (18.8 mmol, 17% unoptimized yield). $^1$H NMR (6:5 ratio of rotamers, 500 MHz, CDCl$_3$), δ 6.61, 6.56 (dd, J=3.7, 3.7 Hz, 1 H total), 6.50 (m, 1 H), 6.15 (m, 1 H), 5.72, 5.71 (d, J=7.0 Hz, 1 H total), 4.81, 4.64 (d, J=11.9 Hz, 1 H total), 4.71 (abq, J=8.0 Hz, 1 H), 3.75, 3.72 (d, J=11.6 Hz, 1 H total), 3.56, 3.46 (br d, J=11.6 Hz, 1 H total), 2.63 (m, 5 H), 1.10 (m, 3 H total); IR (neat): 3049, 2976, 2937, 2879, 1713 (br), 1670, 1636, 1414 cm$^{-1}$; MS m/e (rel int): 357 (4), 355 (18), 353 (55), 351 (M$^+$, 57), 328 (3), 326 (32), 324 (100), 322 (98), 220 (87), 204 (53), 148 (38), 147 (36), 133 (42), 131 (44), 91 (64), 57 (94). Anal. Calcd. for C$_{14}$H$_{16}$NO$_3$Cl$_3$: C, 47.68; H, 4.57; N, 3.97. Found: C, 47.63; H, 4.73; N, 3.78.

EXAMPLE 18

4-Propionyl-6-(2,2,2-trichloroethoxycarbonyl)-6-azabicyclo[3.2.2]non-3-ene [15] (Prepared from 14 in 86% yield using the general procedure described for 9a). $^1$H NMR (400 MHz, CDCl$_3$, 2:1 ratio of rotamers), δ 6.77 (dd, J=4.0, 4.0 Hz, 1 H), 5.22 (br s, 1 H), 4.82, 4.79 (d, J=12.1 Hz, 1 H total), 4.66, 4.57 (d, J=12.1 Hz, 1 H total), 3.80 (br d, J=12.5 Hz, 1 H), 3.52, 3.41 (d, J=12.5 Hz, 1 H total), 2.80-2.57 (m, 4 H), 2.32, 2.28 (m, 1 H total), 2.11 (m, 1 H), 1.95 (m, 1 H), 1.83 (m, 1 H), 1.63 (m, 1 H), 1.10, 1.07 (t, J=7.3 Hz, 3 H total); IR (neat): 2974, 2937, 2873, 1715 (br), 1668, 1416 cm$^{-1}$; MS m/e (rel int): 359 (0.3), 357 (3), 355 (11), 353 (M$^+$, 11), 330 (4), 328 (31), 326 (98), 324 (100), 206 (31), 194 (18), 150 (20), 133 (34), 131 (31), 105 (34), 95 (29), 79 (25), 57 (60). Anal. Calcd. for C$_{14}$H$_{18}$NO$_3$Cl$_3$: C, 47.41; H, 5.12; N, 3.95. Found: C, 47.54; H, 5.19; N, 3.88.

EXAMPLE 19

4-Propionyl-6-azabicyclo[3.2.2]non-3-ene [16] and 6-Benzyl-4-propionyl-6-azabicyclo[3.2.2]non-3-ene [17] A solution of 15 (2.19 g, 6.17 mmol) in 30 mL HOAc was prepared, and Zn (4.0 g) was added. The mixture was stirred under Ar for 3.5 h. The mixture was diluted with water (75 mL) and filtered. The mixture was then neutralized with NaHCO$_3$ (s) and conc aq NH$_4$OH and extracted with CH$_2$Cl$_2$ (5×60 mL). The organic washings were combined, dried (MgSO$_4$), and evaporated to give crude 16 (1.11 g, 100%). A sample of compound 16 was purified by column chromatography (5% Et$_3$N/Et$_2$O with 10% MeOH). $^1$H NMR (500 MHz) δ 6.88 (dd, J=4.3, 4.0 Hz, 1 H), 4.17 (d, J=4.8 Hz, 1 H), 3.18 (ddd, J=11.6, 1.8, 1.8 Hz, 1 H), 2.97 (ddd, J=11.6, 2.1, 2.1 Hz, 1 H), 2.68 (q, J=7.3 Hz, 2 H), 2.73-2.58 (m, 2 H), 2.09 (m, 1 H), 2.06 (br s, 2 H), 1.86 (m, 1 H), 1.74 (m, 1 H), 1.64 (m, 1 H), 1.09 (t, J=7.3 Hz, 3 H); $^{13}$C NMR (125 MHz, CDCl$_3$), δ 201.0, 147.4, 141.6, 46.5, 44.8, 38.8, 30.3, 29.3, 28.1, 23.6, 8.74; IR (neat): 3600-3200 (br), 2971, 2935, 2865, 1664, 1644 cm$^{-1}$; HRMS calcd for C$_{11}$H$_{17}$NO 179.1310; found 179.1320.

EXAMPLE 20

All of crude 16 was dissolved in dry CH$_2$Cl$_2$ and i-Pr$_2$EtN (1.4 mL, 8.0 mmol) was added followed by benzyl bromide (0.81 mL, 6.8 mmol). The reaction mixture was stirred for 12 h, and added to 75 mL Et$_2$O. The reaction mixture was then extracted with 10% aq HCl (3×20 mL). The acid washings were combined, neutralized with NaHCO$_3$ (s) and conc aq NH$_4$OH to pH 10 and extracted with CH$_2$Cl$_2$ (4×40 mL). The organic washings were combined, dried (MgSO$_4$) and evaporated to give the crude benzylated product, which was purified by column chromatography (5% Et$_3$N in 1:1 pentane/Et$_2$O) to give the title product as a light yellow oil. Yield: 1.08 g (4.01 mmol, 65% overall from 15), $^1$H NMR (400 MHz) δ 7.32-7.21 (m, 5 H), 6.93 (dd, J=4.0, 4.0 Hz, 1 H), 4.04 (d, J=6.2 Hz, 1 H), 3.72 (d, J=13.6 Hz, 1 H), 3.40 (d, J=13.2 Hz, 1 H), 2.89 (m, 1 H), 2.75-2.60 (m, 3 H), 2.48 (br d, J=22.0 Hz, 1 H), 2.40 (d, J=10.6 Hz, 1 H), 2.15 (m, 1 H), 2.06 (br s, 1 H), 1.85 (m, 1 H), 1.60 (m, 2 H), 1.10 (t, J=7.3 Hz, 3 H); $^{13}$C NMR (75 MHz, CDCl$_3$), δ 201.7, 144.0, 142.0, 139.6, 128.7, 128.0, 126.6, 60.9, 53.8, 50.6, 38.8, 30.2, 29.1, 28.6, 24.2, 9.0; IR (neat): 3083, 3060, 3027, 2973, 2935, 2863, 2801, 1663, 1637 cm$^{-1}$.

EXAMPLE 21

2-Propionyl-(6-phenoxycarbonyl-6-azabicylo[3.2.2]non-2-ene) [21] (Prepared from 20 in 73% yield using the general procedure described for 9a). $^1$H NMR (8:5 ratio of rotamers, 500 MHz, CDCl$_3$), δ 7.37-7.33 (m, 2 H), 7.21-7.17 (m, 1 H), 7.11 (d, J=7.6 Hz, 2 H), 6.83 (m, 1 H), 4.50, 4.43 (br t, 1 H total), 3.78, 3.70 (ddd, J=12.2, 2.1, 2.1 Hz, 1 H total), 3.66, 3.50 (dd, J=12.2, 3.7 Hz, 1 H total), 3.56-3.50 (m, 1 H), 3.12-3.01 (m, 1 H), 2.72 (m, 2 H), 2.64-2.53 (ddd×2, J=20.4, 2.7, 2.7 Hz, 1 H), 2.25-2.15 (m, 1 H), 2.00-1.80 (m, 3 H), 1.13 (m, 3 H); IR (neat): 3042, 2974, 2938, 2904, 2872, 1717, 1666, 1639 cm$^{-1}$. Anal. Calcd for C$_{18}$H$_{21}$NO$_3$: C, 72.21; H, 7.07; N, 4.68. Found: C, 72.12; H, 7.10; N, 4.64.

EXAMPLE 22

2-Propionyl-(6-methyl-6-azabicylo[3.2.2]non-2-ene) [22] A flask was charged with LiAlH$_4$ (410 mg, 10.8 mmol) and dry THF (20 mL), giving a slurry. A solution of 21 (645 mg, 2.15 mmol) in dry THF (30 mL) was added dropwise with stirring, and the reaction was then heated to reflux for 1 h. The reaction was cooled to room temperature, and quenched with dropwise addition of 50 mL EtOAc. The reaction was diluted with H$_2$O (40 mL) and NaCl (sat, aq, 40 mL), and the layers separated. The aqueous layer was extracted with 2×40 mL EtOAc. The organic layers were combined and extracted with 3×50 mL 10% HCl. The aqueous layers were then combined and neutralized with NaHCO$_3$(s) and basified to pH=12 with NaOH (aq). The aqueous layer was extracted with 3×50 mL CH$_2$Cl$_2$, and the organic layers combined, dried (MgSO$_4$), and evaporated to give 2-(1-hydroxy-1-propyl)-(6-methyl-6-azabicyclo[3.2.2]non-2-ene) as a yellow oil (1:1 ratio of diastereomers). Crude yield: 419 mg, 2.17 mmol, 100%).

Oxidation: Dess-Martin (Method B): All of the above material was dissolved in dry CH$_2$Cl$_2$ (20 mL), and cooled to 0° C. Solid Dess-Martin periodinane (1.15 g, 2.71 mmol) was added, and the reaction stirred for 10 h while warming to room temperature. The reaction was diluted with Et$_2$O (100 mL), and 50 mL 10% NaOH added. The mixture was stirred for 10 min, and the layers separated. The aqueous layer was extracted with 50 mL Et$_2$O, and the organic layers combined, dried (MgSO$_4$), and evaporated to give the crude product, which was purified by column chromatography (5% Et$_3$N in Et$_2$O) to give the title product as a yellow oil. Yield: 258 mg (1.35 mmol, 63% overall for 2 steps). $^1$H NMR (500 MHz, CDCl$_3$), δ 6.80 (dd, J=4.0, 4.0 Hz, 1 H), 3.24 (dd. J=4.3, 4.0 Hz, 1 H), 2.99 (d, J=11.0, 10.7 Hz, 1 H), 2.92 (m, 1 H), 2.87 (m, 1 H), 2.69 (dq, J=7.3, 1.2 Hz, 2 H), 2.62 (d, J=10.7 Hz, 1 H), 2.40 (s, 3 H), 2.24 (ddd, J=19.8, 3.7, 3.7 Hz, 1 H), 2.11 (m, 1 H), 1.91 (m, 1 H), 1.62 (m, 2 H), 1.09 (t, J=7.3 Hz, 3 H); $^{13}$C NMR (125 MHz, CDCl$_3$), δ 200.9, 147.1, 139.9, 58.1, 54.6, 43.1, 33.3, 30.1, 27.7, 25.4, 25.4, 8.8; IR (neat): 3043, 2936, 2874, 2797, 2766, 1668, 1637 cm$^{-1}$. HRMS calcd for C$_{12}$H$_{19}$NO 193.1467; found 193.1459.

EXAMPLE 23

6-Methyl-6-azabicyclo[3.2.2]non-3-ene-7-one)-4-carboxylic acid [25] A solution of 24 (2.65 g, 9.48 mmol) in absolute ethanol (110 mL) was prepared in a Parr™ hydrogenation flask, and (PPh$_3$)$_3$RhCl (201 mg, 0.217 mmol) was added. The flask was flushed with H$_2$ and pressurized to 50 psi. The flask was agitated for 33 h, and the reaction checked by $^1$H NMR. The solvent was removed at reduced pressure to give 2-ethoxy-2-oxoethyl (6-methyl-6-azabicyclo[3.2.2] non-3-ene-7-one)-4-carboxylate (~100% yield) as an orange oil which was used without further purification. $^1$H NMR (CDCl$_3$), δ 7.09 (m, 1 H), 4.70 (abq, J=15.8 Hz, 2 H), 4.42 (m, 1 H), 4.25 (q, J=7.2 Hz, 2 H), 3.00 (s, 3 H), 2.89-2.81 (m, 2 H), 2.49 (m, 1 H), 2.21-1.80 (m, 4 H), 1.30 (t, J=7.2 Hz, 3 H).

All of hydrogenated material isolated above was dissolved in 40 mL methanol, and added to a solution of NaOMe (3.10 g, 57.4 mmol) in methanol (75 mL) at 0° C. The reaction was stirred for 1 h at 0° C., and the solvent partially removed under reduced pressure. A chilled mixture of NaCl (sat, aq, 100 mL) and NH$_4$Cl (sat, aq, 100 mL) was added, and the mixture extracted with 4×60 mL CH$_2$Cl$_2$. The organic layers were combined, dried (MgSO$_4$), and evaporated to give crude methyl (6-methyl-6-azabicyclo[3.2.2]non-3-ene-7-one)-4-carboxylate as a yellow oil, which was used directly in the next step.

All of the above material was subsequently dissolved in a 2:1 mixture of methanol and H$_2$O (75 mL total), and LiOH.H$_2$O (606 mg, 14.4 mmol) added. The reaction was heated to reflux for 11 h. The reaction was allowed to cool to room temperature, diluted with 40 mL H$_2$O, and the dark mixture extracted with 2×40 mL CH$_2$Cl$_2$. The organic washings were combined, back-extracted with H$_2$O (40 mL), and the aqueous washings combined. The aqueous solution was acidified to pH=3, and repeatedly extracted (10×75 mL) with CH$_2$Cl$_2$. The organic washings were dried (MgSO$_4$) and concentrated, giving the title compound (25) as a white powder, which was filtered, washed with CH$_2$Cl$_2$, and dried in vacuo. Yield of white powder: 1.26 g (6.45 mmol, 68% overall from 24). Mp~265° C. (dec). $^1$H NMR (300 MHz, DMSO-d$_6$), δ 6.83 (br s, 1 H), 4.31 (d, J=4.5 Hz, 1 H), 2.83 (s, 3 H), 2.65-2.40 (m, 3 H), 2.14-1.75 (m, 4 H); CO$_2$H not observed; $^{13}$C NMR (75 MHz, DMSO-d$_6$), δ 172.9, 167.6, 141.2, 135.3, 52.9, 39.0, 34.0, 32.8, 29.7, 23.9. Anal Calcd for C$_{10}$H$_{13}$NO$_3$: C, 61.53; H, 6.71; N, 7.18. Found: C, 61.39; H, 6.74; N, 7.15.

EXAMPLE 24

4-Propionyl-6-methyl-6-azabicyclo[3.2.2]non-3-ene-7-one) [26] A slurry of 25 (589 mg, 3.02 mmol) in dry CH$_2$Cl$_2$ (25 mL) was prepared, and SOCl$_2$ (0.50 mL, 6.9 mmol) added. The reaction was heated to reflux for 1.5 h. The yellow solution was evaporated, and the excess SOCl$_2$ was pumped off under vacuum and the crude acid chloride was characterized by $^1$H NMR: $^1$H NMR (400 MHz, CDCl$_3$), δ 7.43 (t, 1 H), 4.42 (br s, 1 H), 3.01 (s, 3 H), 2.95 (m, 1 H), 2.64 (ddd, J=20.8, 4.3, 3.7 Hz, 1 H), 2.20 (m, 2 H), 2.09 (m, 2 H), 1.93 (dd, J=10.4, 7.9 Hz, 1 H).

A flask was charged with CuBr.SMe$_2$ (748 mg, 3.64 mmol) and cooled to −78° C. under argon. A solution of EtMgBr (Aldrich, 3.0 M in Et$_2$O; 2.6 mL, 7.8 mmol) was then added, giving a thick paste. Dry Et$_2$O (10 mL) was added, and a solution of the acid chloride isolated above in dry THF (30 mL) was slowly added over 30 min. The reaction was stirred for 2 h at −78° C., and quenched with 50 mL NH$_4$Cl (sat, aq). The mixture was allowed to stir overnight while warming to rt. Diethyl ether (50 mL), water (50 mL), and 50 mL NaCl (sat, aq) were added, and the layers separated. The aqueous layer was saturated with NaCl (s) and extracted with 4×60 mL EtOAc. The organic layers were combined, back extracted with 100 mL NaCl (sat, aq), dried (MgSO$_4$) and evaporated to give the crude product as a yellow oil. Column chomatography (2:1 EtOAc/hexanes) gave the title compound (25) as a light yellow oil. Yield: 400 mg (1.93 mmol, 64%, 44% overall from 24. $^1$H NMR (500 MHz, CDCl$_3$), δ 6.82 (dd, J=4.3, 3.7 Hz, 1 H), 4.60 (d, J=3.6 Hz, 1 H), 2.94 (s, 3 H), 2.89 (dd, J=20.8, 1.8 Hz, 1 H), 2.81 (m, 1 H), 2.68 (m, 2 H), 2.50 (ddd, J=20.8, 4.3, 4.3 Hz, 1 H), 2.21-2.12 (m, 2 H), 1.95-1.85 (m, 2 H); $^{13}$C NMR (125 MHz, CDCl$_3$), δ 200.1, 174.0, 143.3, 141.0, 51.8, 39.4, 34.7, 33.4, 29.8, 29.7, 24.5, 8.4; IR (neat): 3047, 2938, 2875, 1662, 1640 cm$^{-1}$. HRMS calcd for C$_{12}$H$_{17}$NO$_2$ 207.1259; found 207.1281.

EXAMPLE 25

Synthesis of 6-Methyl-4β-propionyl-3β-(p-tolyl)-6-azabicyclo[3.2.2]nonane [12a] Typical Procedure. A flame-dried flask was charged with CuBr.Me$_2$ (535 mg, 2.60 mmol), and a solution (Aldrich, 1.0 M) of p-TolMgBr in Et$_2$O (5.2 mL, 5.2 mmol) was added. The mixture was stirred at rt for 15 min and cooled to 0° C. under argon. A solution of 4-propionyl-6-methyl-6-azabicyclo[3.2.2]non-3-ene (100 mg, 0.517 mmol) in 10 mL dry THF was added dropwise over 5 min. The reaction was stirred for 24 h while warming to rt. The mixture was cooled to −78° C., and a 1M solution of HCl in Et$_2$O (20 mL) was slowly added while keeping the internal temperature below −70° C. The mixture was allowed to warm to 0° C. and poured into ice water (50 mL). Diethyl ether (50 mL) was added, and the layers separated. The organic layer was extracted with 2×50 mL 10% HCl and the aqueous extracts combined, neutralized with NaHCO$_3$ (s), and basified to pH 11-12 with NH$_4$OH. The aqueous solution was then extracted with 4×75 mL CH$_2$Cl$_2$, dried (MgSO4), and evaporated to give crude 12a. The crude mixture was chromatographed (10:9:1 pentane/Et2O/Et$_3$N (R$_f$=0.65)) to give the title product as a white crystalline solid. Yield: 99 mg (0.35 mmol, 67%). $^1$H NMR (500 MHz, CDCl$_3$), δ 7.22 (d, J=8 Hz, 2 H), 7.03 (d, J=8 Hz, 2 H), 3.31 (dd, J=5.8, 5.5 Hz, 1 H), 3.19 (dd, J=5.8, 5.5 Hz, 1 H), 3.14 (ddd, J=10.7, 2, 2 Hz, 1 H), 3.09 (ddd, J=13.4, 4.8, 4.6 Hz, 1 H), 2.82 (dd, J=13.1, 13.1 Hz, 1 H), 2.46 (dd, J=10.1, 2.7 Hz, 1 H), 2.36 (s, 3 H), 2.35 (m, 1 H), 2.28 (s, 3 H), 2.22 (m, 1 H), 2.11 (br s, 1 H), 2.05 (m, 2 H), 1.82-1.60 (m, 3 H), 0.82 (t, J=7.3 Hz, 3H); $^{13}$C NMR (125 MHz, CDCl$_3$), δ 210.7, 141.3, 134.8, 128.5, 127.9, 62.3, 58.7, 57.8, 45.4, 38.9, 35.3, 35.2, 29.7, 22.1, 20.9, 20.7, 7.6; IR (KBr): 3019, 2943, 1712, 1513 cm$^{-1}$; MS m/e (rel int): 285 (M$^+$, 34), 228 (90), 82 (100). Anal. Calcd for C$_{19}$H$_{27}$NO: C, 79.95; H, 9.53; N, 4.91. Found: C, 79.66; H, 9.57; N, 4.86.

Derivatives 12b-j, 13a-b, 18a-b, 19, 23 and 27 were synthesized using a similar procedure. Yields and characterization data are given for each compound.

EXAMPLE 26

6-Methyl-3β-(2-naphthyl)-4β-propionyl-6-azabicyclo[3.2.2]nonane [12b] (64%) $^1$H NMR (500 MHz, CDCl$_3$), δ 7.79-7.71 (m, 4 H), 7.49 (d, J=8.2 Hz, ☐ H), 7.42-7.37 (m, 2 H), 3.38-3.25 (m, 3 H), 3.19 (br d, J=10.4 Hz, 1 H), 2.96 (dd, J=13, 13 Hz, 1 H), 2.49 (d, J=10.4 Hz, 1 H), 2.38 (s, 3 H), 2.33 (m, 1 H), 2.25 (m, 1 H), 2.16 (m, 2 H), 1.99 (m, 1 H), 1.84 (m, 1 H), 1.76 (m, 1 H), 1.69 (m, 1 H), 0.77 (t, J=7.3 Hz, 3H); $^{13}$C NMR (125 MHz, CDCl$_3$), δ 210.3, 142.0, 133.3, 131.8, 127.8, 127.4, 127.1, 126.5, 125.6, 125.0, 62.3, 58.8, 57.9, 45.4, 39.5, 35.2, 29.7, 22.2, 20.8, 7.6; IR (neat): 3054, 2932, 2868, 2798, 2766, 1715 cm$^{-1}$; MS m/e (rel int): 321 (M$^+$, 41), 264 (100), 110 (21), 96 (47), 82 (86), 57 (30). Anal. Calcd for C$_{22}$H$_{27}$NO: C, 82.20; H, 8.47; N, 4.36. Found: C, 82.02; H, 8.55; N, 4.29.

EXAMPLE 27

3β-(4-Isopropylphenyl)-6-methyl-4β-propionyl-6-azabicyclo[3.2.2]nonane [12c] (29%). This compound was also prepared independently by hydrogenation of the isopropenylphenyl derivative 12f. $^1$H NMR (500 MHz, CDCl$_3$), δ 7.24 (d, J=8.2 Hz, 2 H), 7.11 (d, J=8.2 Hz, 2 H), 3.31 (dd, J=5.8, 5.5 Hz, 1 H), 3.20 (dd, J=5.8, 5.5 Hz, 1 H), 3.14 (dd, J=10.4, 2.5, 2.5 Hz, 1 H), 3.11 (ddd, J=13.1, 4.9, 4.6 Hz, 1 H), 2.85 (m, 2 H), 2.45 (dd, J=10.4, 3.6 Hz, 1 H), 2.36 (s, 3H), 2.35 (m, 1 H), 2.22 (m, 1 H), 2.08 (m, 3 H) 1.78 (m, 1 H), 1.72-1.58 (m 2 H), 1.21 (d, J=7.3 Hz, 6 H), 0.82 (t, J=7.3 Hz, 3 H); $^{13}$C NMR (125 MHz, CDCl$_3$), δ 210.8, 145.8, 141.6, 128.0, 125.9, 62.3, 58.8, 57.9, 45.4, 38.9, 35.3, 35.1, 33.6, 29.7, 24.0, 24.0, 22.2, 20.7, 7.7; IR (KBr): 3026, 2953, 2929, 2913, 2867, 2788, 2756, 1712 cm$^{-1}$; MS m/e (rel int): 313 (M$^+$, 37), 256 (100), 110 (25), 96 (51), 82 (85). Anal. Calcd. for C$_{21}$H$_{31}$NO: C, 80.46; H, 9.97; N, 4.47. Found: C, 80.27; H, 10.00; N, 4.40.

EXAMPLE 28

3β-(4-Chlorophenyl)-6-methyl-4β-propionyl-6-azabicyclo[3.2.2]nonane [12d] (39%) $^1$H NMR (500 MHz, CDCl$_3$), δ 7.27 (d, J=8.2 Hz, 2 H), 7.20 (d, J=8.5 Hz, 2H), 3.33 (dd, J=6.1, 5.5 Hz, 1 H), 3.16 (dd, J=5.8, 5.5 Hz, 1 H), 3.13 (br d, J=10.7 Hz, 1 H), 3.07 (ddd, J=13.4, 5.2, 4.6 Hz, 1 H), 2.81 (dd, J=13.4, 12.8 Hz, 1 H), 2.44 (dd, J=10.4, 3.4 Hz, 1 H), 2.37 (s, 3 H), 2.23 (m, 1 H), 2.11 (br s, 1H), 2.02 (m, 2 H), 1.82-1.58 (m, 4 H), 0.84 (t, J=7.3 Hz, 3 H); $^{13}$C NMR (125 MHz, CDCl$_3$), δ 210.0, 143.0, 131.1, 129.6, 127.8, 62.2, 58.6, 57.8, 45.4, 39.0, 35.1, 35.0, 29.5, 22.1, 20.6, 7.6; IR (KBr): 2986, 2953, 2929, 1712 cm$^{-1}$; MS m/e (rel int): 305 (M$^+$, 28), 248 (100), 110 (29). Anal. Calcd for C$_{18}$H$_{24}$NOCl: C, 70.69; H, 7.91; N, 4.58. Found: C, 70.75; H, 7.96; N, 4.51.

EXAMPLE 29

3β-(4-Ethenylphenyl)-6-methyl-4β-propionyl-6-azabicyclo[3.2.2]nonane [12e] (74%) $^1$H NMR (400 MHz, CDCl$_3$), δ 7.29 (s, 4 H), 6.67 (dd, J=17.6, 11.0 Hz, 1 H), 5.68 (d, J=17.6 Hz, 1 H), 5.17 (d, J=10.6 Hz, 1 H), 3.32 (dd, J=5.8, 5.1 Hz, 1 H), 3.20 (dd, J=5.5, 5.5 Hz, 1 H), 3.11 (m, 2 H), 2.84 (dd, J=13.2, 12.8 Hz, 1 H), 2.45 (dd, J=10.3, 3.3 Hz, 1 H), 2.36 (s, 3 H), 2.22 (m, 1 H), 2.12 (br s, 1 H), 2.04 (m, 1 H), 1.83-1.60 (m, 4 H), 0.82 (t, J=7.3 Hz, 3 H); $^{13}$C NMR (75 MHz, CDCl$_3$), δ 210.4, 144.3, 136.7, 134.8, 128.3, 125.7, 112.8, 62.3, 58.7, 57.8, 45.4, 39.1, 35.1, 35.0, 29.6, 22.1, 20.6, 7.6; IR (KBr): 3080, 3040, 3016, 2999, 2965, 1713, 1624 cm$^{-1}$; MS m/e (rel int): 297 (M$^+$, 11), 240 (35), 181 (12), 131 (21), 119 (21), 110 (8). Anal. Calcd for C$_{20}$H$_{27}$NO: C, 80.76; H, 9.15; N, 4.71. Found: C, 80.80; H, 9.19; N, 4.68.

EXAMPLE 30

6-Methyl-4β-propionyl-3β-(4-isopropenylphenyl)-6-azabicyclo[3.2.2]nonane [12f] (76%) $^1$H NMR (500 MHz, CDCl$_3$), δ 7.36 (d, J=8.2 Hz, 2 H), 7.29 (d, J=8.5 Hz, 2 H), 5.34 (s, 1 H), 5.02 (s, 1 H), 3.33 (dd, J=5.8, 5.2 Hz, 1 H), 3.21 (dd, J=5.8, 5.5 Hz, 1 H), 3.14 (ddd, J=10.6, 2.4, 2.4 Hz, 1 H), 3.12 (ddd, J=13.7, 4.9, 4.6 Hz, 1 H), 2.84 (dd, J=13.1, 12.8 Hz, 1 H), 2.46 (dd, J=10.7, 3.7 Hz, 1 H), 2.37 (s, 3 H), 2.35 (m, 1 H), 2.23 (m, 1 H), 2.12 (br s, 3 H), 2.10-1.97 (m, 3 H), 1.83-1.62 (m, 3 H), 0.83 (t, J=7.3 Hz, 3 H); $^{13}$C NMR (125 MHz, CDCl$_3$), δ 210.4, 143.8, 143.0, 138.2, 128.0, 124.9, 111.5, 62.3, 58.7, 57.9, 45.4, 39.1, 35.2, 35.1, 29.6, 22.2, 21.8, 20.7, 7.7; IR (KBr): 3088 ; 2959, 2931, 1711, 1622 cm$^{-1}$; MS m/e (rel int): 311 (M$^+$, 0.6), 281 (2.7), 254 (1.6), 181 (12), 169 (10), 131 (28), 119 (22), 100 (10), 69 (100). Anal. Calcd for C$_{21}$H$_{29}$NO: C, 80.98; H, 9.38; N, 4.50. Found: C, 80.95; H, 9.42; N, 4.47.

EXAMPLE 31

2α,6-Dimethyl-4β-propionyl-3β-(p-tolyl)-6-azabicyclo[3.2.2]nonane [12g] (55%) $^1$H NMR (500 MHz, CDCl$_3$), δ 7.18 (d, J=7.9 Hz, 2 H), 7.02 (d, J=7.9 Hz, 2 H), 3.32 (dd, J=6.4, 6.4 Hz, 1 H), 3.23 (ddd, J=11.0, 2.1, 1.8 Hz, 1 H), 3.11 (m, 1 H), 3.07 (dd, J=7.0, 5.2 Hz, 1 H), 2.63 (dd, J=11.3, 5.8 Hz, 1 H), 2.57 (dd, J=11.9, 4.9 Hz, 1 H), 2.38 (s, 3 H), 2.38 (m, 1 H), 2.28 (s, 3 H), 2.21 (m, 1 H), 1.85 (m, 2 H), 1.71 (m, 2 H), 1.55 (m, 1 H), 0.81 (d, J=6.7 Hz, 3 H), 0.80 (t, J=3 H); $^{13}$C NMR (125 MHz, CDCl$_3$), δ 210.6, 140.0, 134.9, 129.7, 128.4, 63.3, 58.4, 56.9, 47.7, 45.0, 38.5, 37.0, 35.8, 21.4, 21.04, 20.99, 17.6, 7.7; IR (neat): 2967, 2933, 2870, 2803, 2766, 1716 cm$^{-1}$; MS m/e (rel int): 299 (M$^+$, 22), 242 (41), 124 (23), 96 (100). Anal. Calcd for C$_2$OH$_{29}$NO: C, 80.22; H, 9.76; N, 4.68. Found: C, 80.05; H, 9.72; N, 4.57.

EXAMPLE 32

6-Methyl-2α-phenyl-4β-propionyl-3β-(p-tolyl)-6-azabicyclo[3.2.2]nonane [12h] (39%) Mp=172-173° C. $^1$H NMR (500 MHz, CDCl$_3$), δ 7.16-7.11 (m, 4 H), 7.07 (d, J=8.0 Hz, 2 H), 7.02 (t, J=6.8 Hz, 1 H), 6.84 (d, J=7.7 Hz, 2 H), 4.46 (d, J=12.6Hz, 1 H), 3.51 (dd, J=12.6, 4.8 Hz, 1 H), 3.45 (d, J=12.8 Hz, 1 H), 3.42 (dd, J=6.5, 6.0 Hz,1 H), 3.31 (dd, J=6.8, 5.0 Hz, 1 H), 2.64 (dd, J=11.1, 5.3 Hz, 1 H), 2.43 (m, 1 H), 2.42 (s, 3 H), 2.31 (m, 1 H), 2.14 (s, 3 H), 1.92 (m, 4 H), 1.43 (m, 1 H), 0.83 (t, J=7.3 Hz, 3 H); Irradiation of H(4)$_{axial}$ (4.46 ppm) gives an nOe enhancement to one of the bridgehead methylenes adjacent to the nitrogen (3.45 ppm) and to H (1); $^{13}$C NMR (125 MHz, CDCl$_3$), δ 210.4, 146.8, 138.9, 134.37, 129.7, 128.1 (overlap), 127.6, 125.3, 63.2, 58.4, 57.6, 49.7, 45.1, 42.6, 39.2, 35.7, 20.9, 20.7, 17.8, 7.7; IR (KBr): 3020, 2964, 2932, 2917, 1708 cm$^{-1}$; MS m/e (rel int): 361

(M+, 5), 304 (4), 187 (76), 158 (100), 96 (54). Anal. Calcd for $C_{25}H_{31}NO$: C, 83.06; H, 8.64; N, 3.87. Found: C, 82.79; H, 8.67; N, 3.83.

EXAMPLE 33

1,2α,6-Trimethyl-4β-propionyl-3β-(p-tolyl)-6-azabicyclo[3.2.2]nonane [12i] (34%) $^1$H NMR (500 MHz, CDCl$_3$), δ 7.16 (d, J=7.9 Hz, 2 H), 7.02 (d, J=7.9 Hz, 2 H), 3.39 (dd, J=6.7, 6.7 Hz, 1 H), 3.22 (d, J=11.9 Hz, 1 H), 3.09 (dd, J=5.5, 4.5 Hz, 1 H), 2.78 (m, 1 H), 2.60 (dd, J=11.9, 4.9 Hz, 1 H), 2.40 (s, 3 H), 2.40 (m, 2 H, overlap), 2.27 (s, 3 H), 2.19 (br t, 1 H), 1.85 (m, 2 H), 1.68 (m, 1 H), 1.26 (m, 1 H), 0.89 (s, 3 H), 0.79 (t, J=7.3 Hz, 3 H), 0.68 (d, J=6.7 Hz, 3 H); $^{13}$C NMR (125 Hz, CDCl$_3$), δ 210.6, 140.9, 134.8, 129.6, 128.4, 64.2, 62.3, 57.6, 48.7, 45.2, 42.8, 35.7, 34.3, 29.8, 24.0, 20.9, 20.4, 16.9, 7.1; IR (neat): 3090, 2971, 2932, 1716 cm$^{-1}$; MS m/e (rel int): 313 (M+, 57), 256 (23), 129 (100). Anal. Calcd. for $C_{21}H_3$,NO.0.25 H$_2$O: C, 79.32; H, 9.98; N, 4.41. Found: C, 79.61; H, 9.87; N, 4.23.

EXAMPLE 34

1,6-Dimethyl-2α-phenyl-4β-propionyl-3β-(p-tolyl)-6-azabicyclo[3.2.2]-nonane [12j] (38%) Mp=141-144° C. $^1$H NMR (500 MHz, CDCl$_3$), δ 7.08 (m, 6 H), 6.97 (t, J=7.0 Hz, 1 H), 6.78 (d, J=7.9 Hz, 2 H), 4.09 (d, J=12.8 Hz, 1 H), 3.51 (dd, J=12.5, 4.9 Hz, 1 H), 3.47 (dd, J=6.7, 6.7 Hz, 1 H), 3.32 (dd, J=11.6, 2.4 Hz, 1 H), 3.24 (dd, J=6.7, 6.7 Hz, 1 H), 2.46 (m, 1 H), 2.44 (s, 3 H), 2.39 (d, J=11.6 Hz, 1 H), 2.32 (m, 1 H), 2.13 (m, 1 H), 2.10 (s, 3 H), 1.95 (ddd, J=13.0, 13.0, 5.5 Hz, 1 H), 1.90 (m, 1 H), 1.28 (ddd, J=13.0, 13.0, 5.5 Hz, 1 H), 0.82 (t, J=7.3 Hz, 3 H), 0.42 (s, 3 H); Irradiation of H(4)$_{axial}$ (4.09 ppm) gives an nOe enhancement of one of the bridgehead methylene protons (3.32 ppm); $^{13}$C (125 MHz, CDCl$_3$), δ 210.5, 144.6, 139.4, 134.2, 132.7 (br), 130.0, 127.8, 127.4 (br), 125.5, 65.4, 62.8, 57.8, 54.6, 45.7, 45.4, 35.8, 35.7, 31.2, 26.4, 20.9, 20.5, 7.7; IR (KBr): 3082, 3058, 3024, 2982, 2966, 1713 cm$^{-1}$; MS m/e (rel int): 375 (M+, 5), 318 (4), 201 (21), 172 (39), 110 (100). Anal. Calcd for $C_{26}H_{33}NO$: C, 83.15; H, 8.86; N, 3.73. Found: 83.00; H, 8.84; N, 3.66.

EXAMPLE 35

6-Methyl-4α-propionyl-3β-(p-tolyl)-6-azabicyclo[3.2.2]nonane [13a] Prepared by the general procedure for the preparation of 12a but using a room temperature quench of the reaction mixture. (12%). $^1$H NMR (500 MHz, CDCl$_3$), δ 7.11 (d, J=8.0 Hz, 2 H), 7.05 (d, J=8.0 Hz, 2 H), 3.31 (m, 2 H), 3.04 (dd, J=10.7, 5.8 Hz, 1 H), 2.69 (d, J=5.8 Hz, 1 H), 2.66 (d, J=10.7 Hz, 1 H), 2.51 (s, 3 H), 2.34 (m, 2 H), 2.29 (s, 3 H), 2.10 (m, 3 H), 1.98-1.70 (m, 5 H), 0.75 (t, J=7.0 Hz, 3 H); $^{13}$C NMR (75 MHz, CDCl$_3$), δ 212.8, 141.9, 135.7, 129.1, 127.7, 58.6, 57.8, 57.7, 44.3, 43.8, 40.6, 36.6, 29.9, 21.9, 21.4, 20.9, 7.3; IR (neat): 3020, 2930, 2920, 2873, 2790, 1701 cm$^{-1}$; MS m/e (rel int): 285 (M+, 24), 228 (100), 110 (25). Anal. Calcd. for $C_{19}H_{27}NO$: C, 79.95; H, 9.53; N, 4.91. Found: C, 80.07; H, 9.42; N, 5.00.

EXAMPLE 36

6-Methyl-3β-(2-naphthyl)-4α-propionyl-6-azabicyclo[3.2.2]nonane [13b] (20%) Isolated via chromatography from a large scale reaction used to prepare 12b using a low temperature quench. $^1$H NMR (500 MHz, CDCl$_3$), δ 7.76 (m, 3 H), 7.66 (s, 1 H), 7.41 (m, 3 H), 3.55 (ddd, J=12.5, 11.9, 4.6 Hz, 1 H), 3.47 (d, J=11.9 Hz, 1 H), 3.05 (dd, J=10.7, 5.2 Hz, 1 H), 2.74 (m, 1 H), 2.55 (s, 3 H), 2.35 (m, 1 H), 2.14 (m, 3 H), 1.94 (m, 1 H), 1.84 (m, 2 H), 1.75 (m, 1 H), 0.68 (t, J=7.3 Hz, 3 H); $^{13}$C NMR (125 MHz, CDCl$_3$), δ 212.6, 142.4, 133.5, 132.2, 128.0, 127.7, 127.5, 126.4, 126.3, 125.9, 125.3, 58.6, 58.0, 57.9, 44.0, 43.9, 41.1, 36.5, 30.0, 21.8, 21.5, 7.3; IR (neat): 3051, 2933, 2908, 1707 cm$^{-1}$; MS m/e (rel int): 321 (M+, 41), 264 (100), 110 (17). Anal. Calcd for $C_{22}H_{27}NO$: C, 82.20; H, 8.47; N, 4.36. Found: C, 82.21; H, 8.39; N, 4.41.

EXAMPLE 37

4β-Propionyl-3α-(p-tolyl)-6-azabicyclo[3.2.2]nonane [18a] (45%) $^1$H NMR (400 MHz, CDCl$_3$), δ 7.10 (d, J=8.0 Hz, 2 H), 7.06 (d, J=8.0 Hz, 2 H), 3.40 (ddd, J=12.5, 5.5, 5.5 Hz, 1 H), 3.29 (d, J=11.4 Hz, 1 H), 3.08 (dd, J=11.4, 4.0 Hz, 1 H), 3.00 (m, 2 H), 2.30 (s, 3 H), 2.28-2.10 (m, 4 H), 2.06 (br s, 1 H), 1.96-1.66 (m, 5 H), 0.73 (t, J=7.0 Hz, 3 H); $^{13}$C NMR (75 MHz, CDCl$_3$), δ 215.0, 141.3, 135.9, 129.2, 127.6, 65.2, 49.7, 44.7, 43.2, 41.7, 36.9, 29.2, 28.8, 26.0, 20.9, 7.1; IR (neat) 3368, 3018, 2932, 1701 cm$^{-1}$; MS m/e (rel int): 271 (M+, 36), 214 (100). Anal. Calcd for $C_{18}H_{25}NO$: C, 79.66; H, 9.28; N, 5.16. Found: C, 79.60; H, 9.29; N, 5.06.

EXAMPLE 38

4β-Propionyl-3α-(4-isopropenylphenyl)-6-azabicyclo[3.2.2]nonane [18b] (70%) $^1$H NMR (500 MHz, CDCl$_3$), δ 7.38 (d, J=8.0 Hz, 2 H), 7.18 (d, J=8.0 Hz, 2 H), 5.35 (s, 1 H), 5.05 (s, 1 H), 3.45 (ddd, J=12.5, 12.2, 5.5 Hz, 1 H), 3.30 (d, J=11.6 Hz, 1 H), 3.09 (dd, J=11.3, 3.7 Hz, 1 H), 3.01 (m, 2 H), 2.31-2.15 (m, 3 H), 2.13 (s, 3 H), 2.07 (br s, 1 H), 1.96-1.67 (m, 6 H), 0.74 (t, J=7.3 Hz, 3 H); $^{13}$C NMR (125 MHz, CDCl$_3$), δ 214.7, 143.6, 142.7, 139.1, 127.6, 125.5, 111.9, 65.1, 49.8, 44.7, 43.0, 41.6, 39.9, 29.2, 28.9, 26.0, 21.7, 7.1; IR (neat): 3367, 3084, 3025, 2971, 1702 cm$^{-1}$; MS m/e (rel int): 297 (M+, 33), 240 (100). Anal. Calcd for $C_{20}H_{27}NO$: C, 80.76; H, 9.15; N, 4.71. Found: C, 80.60; H, 9.29; N, 4.55.

EXAMPLE 39

4β-Propionyl-3β-(p-tolyl)-6-azabicyclo [3.2.2]nonane [19] Prepared from hydrogenation of 6-benzyl-4β-propionyl-3β-p-tolyl-6-azabicyclo[3.2.2]nonane, obtained from 17 in 43% yield using the standard procedure described for 12a. Characterization of the N-benzyl derivative: $^1$H NMR (400 MHz, CDCl$_3$), δ 7.22 (m, 7 H), 7.06 (d, J=8.0 Hz, 2 H), 3.78 (s, 2 H), 3.52 (dd, J=6.2, 5.9 Hz, 1 H), 3.24 (dd, J=5.9, 5.5 Hz, 1 H), 3.09 (m, 2 H), 2.87 (dd, J=13.2, 13.1 Hz, 1 H), 2.41 (dd, J=11.0, 4.0 Hz, 1 H), 2.29 (s, 3 H), 2.28 (m, 1 H), 2.10 (br s, 1 H), 2.06-1.60 (m, 6 H), 0.80 (t, J=7.3 Hz, 3 H); $^{13}$C NMR (75 MHz, CDCl$_3$), δ 210.3, 141.2, 139.7, 134.9, 128.5, 128.4, 128.2, 128.1, 126.7, 63.0, 61.9, 57.6, 56.4, 39.2, 35.6 (2 C), 29.4, 22.1, 21.5, 20.9, 7.4; IR (neat): cm$^{-1}$; MS m/e (rel int): 361 (M+, 12), 304 (66), 186 (13), 172 (25), 158 (41), 91 (100). Anal. Calcd for $C_{25}H_{31}NO$: C, 83.06; H, 8.64; N, 3.87. Found: C, 82.84; H, 8.71; N, 3.95.

EXAMPLE 40

A solution of 6-benzyl-4β-propionyl-3β-p-tolyl-6-azabicyclo[3.2.2]nonane (286 mg, 0.791 mmol) in 50 mL absolute ethanol was prepared in a Parr™ hydrogenation flask, and 10% Pd/C (140 mg) was added. The flask was flushed with H$_2$, and pressurized to 55 psi and agitated for 3 h. The mixture was filtered through Celite, and the filter cake washed several times with ethanol. The solvent was removed under reduced pressure and the crude product chromatographed (85:10:5 Et$_2$O/MeOH/Et$_3$N) to give the title compound as a light yellow solid. Yield: 82 mg (0.30 mmol, 38%). $^1$H NMR (400 MHz, CDCl$_3$), δ 7.12 (d, J=8.1 Hz, 2 H), 7.06 (d, J=8.1 Hz, 2 H), 3.36 (dd, J=4.8, 4.8 Hz, 1 H), 3.29 (dd, J=5.5, 5.1 Hz, 1 H), 3.22 (ddd, J=13.6, 6.0, 4.8 Hz, 1 H), 3.07 (br s, 2 H), 2.60 (dd, J=13.6, 13.6 Hz, 1 H), 2.42 (br s, 1 H), 2.29 (s, 3 H), 2.18 (m, 3 H), 1.99 (m, 1 H), 1.86 (m, 1 H), 1.79 (m, 2 H), 1.67 (m, 1 H), 0.69 (t, J=7.3 Hz, 3 H); $^{13}$C NMR (75 MHz, CDCl$_3$), δ 214.5, 140.0, 135.7, 128.8, 128.0, 62.7, 48.9, 48.8, 40.6, 38.6, 36.3, 29.7, 24.8, 21.4, 20.9, 7.0; IR (neat): 3360, 3045, 3010, 2933, 2865, 1711, 1701 cm$^{-1}$; MS m/e (rel int): 271 (M$^+$, 24), 242 (2), 214 (100). Anal. Calcd for C$_{18}$H$_{25}$NO: C, 79.66; H, 9.28; N, 5.16. Found: C, 79.78; H, 9.32; N, 5.13.

EXAMPLE 41

6-Methyl-2α-propionyl-3β-(p-tolyl)-6-azabicyclo[3.2.2]nonane [23] (25%); $^1$H NMR (500 MHz, CDCl$_3$), δ 7.12 (d, J=7.9 Hz, 2 H), 7.05 (d, J=8 Hz, 2 H), 3.33 (ddd, J=12.2, 12.2, 5.5 Hz, 1 H), 3.06 (d, J=11.9 Hz, 1 H), 3.05 (d, J=11.3 Hz, 1 H), 2.87 (dd, J=6.1, 5.5 Hz, 1 H), 2.81 (d, J=11.0 Hz, 1 H), 2.44 (s, 3 H), 2.32 (m, 1 H), 2.29 (s, 3 H), 2.10-1.96 (m, 3 H), 1.94 (dd, J=5.5, 4.9 Hz, 1 H), 1.87-1.75 (m, 3 H), 1.59 (m, 1 H), 0.75 (t, J=7.0 Hz, 3 H); $^{13}$C NMR (125 MHz, CDCl$_3$), δ 212.9, 140.5, 136.0, 129.2, 127.8, 61.5, 58.3, 56.6, 43.6, 40.3, 38.3, 36.9, 31.8, 21.9, 21.0, 18.7, 7.3; IR (neat): 3018, 2934, 2791, 2764, 1710 cm$^{-1}$; MS m/e (rel int): 285 (M$^+$, 41), 228 (44), 96 (100). Anal. Calcd for C$_{19}$H$_{27}$NO: C, 79.95; H, 9.53; N, 4.91. Found: C, 79.77; H, 9.58; N, 4.80.

EXAMPLE 42

6-Methyl-4β-propionyl-3β-(p-tolyl)-6-azabicyclo[3.2.2]nonan-7-one [27] (29%). $^1$H NMR (500 MHz, CDCl$_3$) δ 7.06 (s, 4 H), 3.83 (dd, J=5.8, 5.5 Hz, 1 H), 3.26 (ddd, J=13.1. 5.2, 5 Hz, 1 H), 3.20 (dd, J=5.2, 5.2 Hz, 1 H), 2.91 (dd, J=6.7, 5.8 Hz, 1 H), 2.80 (d, J=13.4 Hz, 1H, partially overlapped), 2.75 (s, 3 H), 2.29 (s, 3 H), 2.29 (m, 1H, overlap), 2.19 (m, 1 H), 1.95-2.08 (m, 3 H), 1.78-1.90 (m, 2 H), 0.74 (t, J=7.2 Hz, 3 H); $^{13}$C NMR (125 MHz, CDCl$_3$) δ 210.1, 175.1, 138.9, 136.1, 129.0, 127.8, 58.1, 57.5, 40.3, 40.0, 38.4, 34.9, 29.1, 25.3, 21.3, 20.9, 7.2. Anal. Calcd for C$_{19}$H$_{25}$NO$_2$: C, 76.22; H, 8.38; N, 4.61. Found: C, 75.97; H, 8.38; N, 4.61.

EXAMPLE 43

This Example provides a characterization of the receptor binding properties of the compounds of the invention. Binding of tropane analogs at biogenic amine transporters was determined using conventional methods using striatum and frontal cortex dissected from frozen Sprague-Dawley rat brains (Pel-Freez, Rogers, Ark.). Affinities of analogs at dopamine transport sites were determined by displacement of [$^{125}$I]RTI-55 binding in membranes from rat striatum, using 0.5 mg (original wet weight) of membranes and 10 pM [$^{125}$I] RTI-55. Non-specific binding was determined in the presence of 1 μM WF-23 (analog 3a). Affinities of analogs at 5-HT transport sites were determined by displacement of [$^3$H]paroxetine binding in membranes from rat frontal cortex, using 50 mg (original wet weight) of membranes and 0.4 nM [$^3$H] paroxetine. Non-specific binding was determined in the presence of 10 μM fluoxetine. Binding of analogs at norepinephrine transport sites was determined by displacement of [$^3$H]nisoxetine binding in membranes from rat forebrain, using 0.7 nM [$^3$H]nisoxetine. Non-specific binding was determined in the presence of 1 μM desipramine.

Potencies were calculated from displacement curves using 7-10 concentrations of unlabeled analogs, as analyzed by non-linear curve fitting. Because binding of tropanes at dopamine transporters is generally regarded as multiphasic, potencies in inhibiting [$^{125}$I]RTI-55 binding are reported as IC$_{50}$ values. For [$^3$H]paroxetine and [$^3$H]nisoxetine binding assays, K$_i$ values were calculated using the Cheng-Prusoff equation. All data are mean values±S.E.M. of at least three separate experiments, each of which was conducted in triplicate.

The binding studies of a series of 6-azabicyclo[3.2.2]nonane derivatives with varying substitution patterns and stereochemistry of the aryl and carbonyl substituents are summarized in Table 1. Azabicyclononane analogs 12, 13, 18, 19, 23 and 27 were assayed for binding for both the DAT and the SERT and compared to the corresponding tropane derivatives (Table 2). In most cases, the azabicyclononane derivatives show more potent binding than is observed for cocaine at both transporters. When compared to the corresponding tropane system, the N-methyl derivatives (12a-f) show about an order of magnitude lower activity. Added substitution at C(1) and C(2) (12g-j) results in significant loss of potency. As observed in the tropane system, the naphthyl analogue 12b has the strongest binding affinity, while the isopropenylphenyl analogue 12f is the most selective for SERT. The trans-isomers 13a and 23 have very low binding affinity and so does the azabicylononanone 27. The most interesting compounds are the chair-flipped structures 18a and 18b because they show relatively strong binding at both transporters despite the normally inactive trans-arrangement of the C(3) and C(4) substituents. Furthermore, the isopropenylphenyl derivative 18b shows approximately a 50:1 selectivity for SERT. This biological data indicates that the 6-azabicylo[3.2.2]nonane system is a promising entity for the development of therapeutic agents for CNS disorders, such as for the treatment of drug addiction.

TABLE 1

| Cpd | R$_1$ | R$_2$ | Ar | Yield | Binding (nM) DAT | Binding (nM) SERT | Ratio SERT/DAT |
|---|---|---|---|---|---|---|---|
| 12a | H | H | p-tolyl | 67 | 117 ± 13 | 2230 ± 410 | 19 |
| 12b | H | H | 2-napthyl | 40 | 2.8 ± 0.5 | 13.4 ± 2.3 | 4.8 |
| 12c | H | H | 4-i-PrPh | 29 | 7500 ± 1800 | 1760 ± 280 | 0.23 |
| 12d | H | H | 4-ClPh | 39 | 38.1 ± 0.5 | 860 ± 330 | 23 |
| 12e | H | H | 4-(C$_6$H$_4$)CH=CH$_2$ | 74 | 75 ± 24 | 116 ± 30 | 1.9 |
| 12f | H | H | 4-(C$_6$H$_4$)C(Me)=CH$_2$ | 76 | 880 ± 210 | 32.8 ± 9.2 | 0.03 |
| 12g | Me | Me | p-tolyl | 55 | 1830 ± 170 | >2500 | — |
| 12h | Me | Ph | p-tolyl | 39 | 4100 ± 1300 | >2500 | — |
| 12i | | Me | p-tolyl | 34 | 2140 ± 180 | >2500 | — |
| 12j | | Ph | p-tolyl | 38 | 5600 ± 1600 | >2500 | — |

TABLE 1-continued

| Cpd | R₁ | R₂ | Ar | Yield | Binding (nM) DAT | Binding (nM) SERT | Ratio SERT/DAT |
|---|---|---|---|---|---|---|---|
| 13a | H | H | p-tolyl | 12 | 1160 ± 240 | >2500 | — |
| 13b | H | H | 2-naphthyl | 17 | 20.8 ± 4.3 | 6.2 ± 0.5 | 0.3 |
| 18a | | | p-tolyl | 45 | 187 ± 55 | 469 ± 32 | 2.5 |
| 18b | | | 4-(C₆H₄)C(Me)=CH₂ | 70 | 370 ± 170 | 6.48 ± 0.38 | 0.02 |
| 19 | | | p-tolyl | 16 | 24.9 ± 5.6 | 156 ± 26 | 6.3 |
| 23 | | | p-tolyl | 17 | 4700 ± 900 | >2500 | — |
| 27 | | | p-tolyl | 29 | 7,000 ± 1100 | >2500 | — |

₁All compounds tested as their racemates.

The foregoing description of the specific embodiments is for the purpose of illustration and is not to be construed as restrictive. From the teachings of the present invention, those skilled in the art will recognize that various modifications and changes may be made without departing from the spirit of the invention.

What is claimed is:

1. A compound having the following structure:

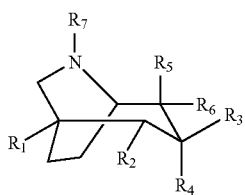

or its enantiomer or racemic mixtures thereof,
wherein the compound is selected from the group of a compound wherein R1, R2 and R4 and R6 are hydrogen, R3 is 2-naphthyl, R5 is —COEt, and R7 is methyl; a compound wherein R1, R2, R4 and R6 are hydrogen, R3 is 4-i-PrPh, R5 is —COEt, and R7 is methyl; a compound wherein R1, R2, R4 and R6 are hydrogen, R3 is 4-ClPh, R5 is —COEt, and R7 is methyl; a compound wherein R1, R2, R4 and R6 are hydrogen, R3 is 4-(C₆H₄)CH=CH₂, R5 is —COEt, and R7 is methyl; a compound wherein R1, R2, R4 and R6 are hydrogen, R3 is 4-(C₆H₄)C(Me)=CH₂, R5 is —COEt, and R7 is methyl; a compound wherein R1 is hydrogen, R2 is methyl, R4 and R6 are hydrogen, R3 is p-tolyl, R5 is —COEt, and R7 is methyl; a compound wherein R1 is hydrogen, R2 is phenyl, R4 and R6 are hydrogen, R3 is p-tolyl, R5 is —COEt, and R7 is methyl; a compound wherein R1, R2 and R7 are methyl, R3 is p-tolyl, R4 and R6 are hydrogen, and R5 is —COEt; a compound wherein R1 and R7 are methyl, R2 is phenyl, R3 is p-tolyl, R4 is hydrogen, R5 is —COEt, and R6 is hydrogen; a compound wherein R1, R2, R4 and R5 are hydrogen, R3 is 2-naphthyl, R6 is —COEt, and R7 is methyl; and, a compound wherein R1, R2, R4, R6 and R7 are hydrogen, R3 is p-tolyl, and R5 is —COEt.

2. A compound as in claim 1, wherein R1, R2 and R4 and R6 are hydrogen, R3 is 2-naphthyl, R5 is —COEt, and R7 is methyl.

3. A compound as in claim 1, wherein R1, R2, R4 and R6 are hydrogen, R3 is 4-i-PrPh, R5 is —COEt, and R7 is methyl.

4. A compound as in claim 1, wherein R1, R2, R4 and R6 are hydrogen, R3 is 4-ClPh, R5 is —COEt, and R7 is methyl.

5. A compound as in claim 1, wherein R1, R2, R4 and R6 are hydrogen, R3 is 4-(C$_6$H$_4$)CH=CH$_2$, R5 is —COEt, and R7 is methyl.

6. A compound as in claim 1, wherein R1, R2, R4 and R6 are hydrogen, R3 is 4-(C6H4)C(Me)=CH$_2$, R5 is —COEt, and R7 is methyl.

7. A compound as in claim 1, wherein R1 is hydrogen, R2 is methyl, R4 and R6 are hydrogen, R3 is p-tolyl, R5 is —COEt, R7 is methyl.

8. A compound as in claim 1, wherein R1 is hydrogen, R2 is phenyl, R4 and R6 are hydrogen, R3 is p-tolyl, R5 is —COEt, R7 is methyl.

9. A compound as in claim 1, wherein R1, R2 and R7 are methyl, R3 is p-tolyl, R4 and R6 are hydrogen, R5 is —COEt.

10. A compound as in claim 1, wherein R1 and R7 are methyl, R2 is phenyl, R3 is p-tolyl, R4 is hydrogen, R5 is —COEt, R6 is hydrogen.

11. A compound as in claim 1, wherein R1, R2, R4 and R5 are hydrogen, R3 is 2-naphthyl, R6 is —COEt, R7 is methyl.

12. A compound as in claim 1, wherein R1, R2, R4, R6 and R7 are hydrogen, R3 is p-tolyl, R5 is —COEt.

13. A compound having the following structure:

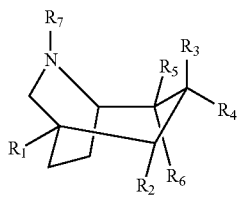

or its enantiomer or racemic mixtures thereof, wherein R1, R2, R3, R6 and R7 are hydrogen, R4 is 4-(C$_6$H$_4$)C(Me)=CH$_2$, R5 is —COEt.

14. A compound having the following structure:

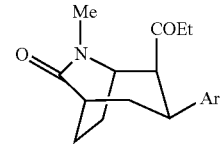

or its enantiomer or racemic mixtures thereof, where Ar is a substituted or unsubstituted phenyl group, wherein the ring substituents, if present, are present as mono-, di- or tri-substitutions comprised of substituents selected from the group consisting of alkyl, alkenyl, alkoxy, halo, nitro, cyano, keto, amino, carboxylate or a combination thereof.

15. A compound as in claim 14, wherein Ar is selected from the group consisting of p-tolyl, 2-naphthyl, 4-i-PrPh, 4-ClPh, 4-(C$_6$H$_4$)CH=CH$_2$, or 4-(C$_6$H$_4$)C(Me)=CH$_2$.

16. A compound having the following structure:

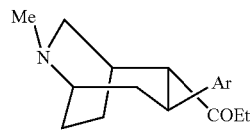

or its enantiomer or racemic mixtures thereof, where Ar is selected from the group consisting of 2-naphthyl, 4-i-PrPh, 4-ClPh, 4-(C$_6$H$_4$)CH=CH$_2$, or 4-(C$_6$H$_4$)C(Me)=CH$_2$.

* * * * *

UNITED STATES PATENT AND TRADEMARK OFFICE
CERTIFICATE OF CORRECTION

PATENT NO. : 7,550,588 B2
APPLICATION NO. : 11/716816
DATED : June 23, 2009
INVENTOR(S) : Davies Page 1 of 1

It is certified that error appears in the above-identified patent and that said Letters Patent is hereby corrected as shown below:

Claim 14, line 7, "or" -- should be -- "and"

Claim 15, line 3, "or" -- should be -- "and"

Claim 16, line 4, "or" -- should be -- "and"

Signed and Sealed this

Eighth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,550,588 B2
APPLICATION NO. : 11/716816
DATED : June 23, 2009
INVENTOR(S) : Davies Page 1 of 1

It is certified that error appears in the above-identified patent and that said Letters Patent is hereby corrected as shown below:

Column 28, Claim 14, line 18, "or" -- should be -- "and"

Column 28, Claim 15, line 21 "or" -- should be -- "and"

Column 28, Claim 16, line 34, "or" -- should be -- "and"

This certificate supersedes the Certificate of Correction issued September 8, 2009.

Signed and Sealed this

Twenty-ninth Day of September, 2009

David J. Kappos
*Director of the United States Patent and Trademark Office*